US010687455B2

(12) United States Patent
Boyce et al.

(10) Patent No.: US 10,687,455 B2
(45) Date of Patent: Jun. 23, 2020

(54) SYSTEMS AND PROCESSES FOR COMBINING DIFFERENT TYPES OF SEEDS

(71) Applicant: Monsanto Technology LLC, St. Louis, MO (US)

(72) Inventors: Gregory A. Boyce, Wentzville, MO (US); Jeffrey Scot Davis, O'Fallon, MO (US); James E. Fuhrman, Ballwin, MO (US); David Kelpe, Washington, MO (US); Michael Krejcarek, Glendale, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/977,602

(22) Filed: May 11, 2018

(65) Prior Publication Data
US 2018/0255697 A1 Sep. 13, 2018

Related U.S. Application Data

(62) Division of application No. 13/318,592, filed as application No. PCT/US2010/033132 on Apr. 30, 2010, now Pat. No. 9,980,423.
(Continued)

(51) Int. Cl.
*A01C 1/00* (2006.01)
*A01N 65/00* (2009.01)
(Continued)

(52) U.S. Cl.
CPC ............... *A01C 1/00* (2013.01); *A01N 65/00* (2013.01); *A01N 2300/00* (2013.01);
(Continued)

(58) Field of Classification Search
CPC .... A01C 1/00; A01C 7/00; A01C 7/04; A01C 7/08; A01C 7/10; A01C 7/16; A01C 7/18;
(Continued)

(56) References Cited

U.S. PATENT DOCUMENTS 2,530,501 A * 11/1950 Avril ........................ B28C 5/04
366/141
2,863,651 A * 12/1958 McBride ............. B01F 15/0483
177/70
(Continued)

FOREIGN PATENT DOCUMENTS

DE 19 19 606 A1 11/1970
DE 22 08 225 A1 8/1973
(Continued)

OTHER PUBLICATIONS

Bruce Tabashnik, Delaying insect adaptation to transgenic plants: see mixtures and refugia reconsidered, Proc R. Soc. Lond. B (1994), 255, 7-12. (Year: 1994).*
(Continued)

*Primary Examiner* — Anne Marie Grunberg
(74) *Attorney, Agent, or Firm* — Harness, Dickey & Pierce, P.L.C.

(57) ABSTRACT

A process and system are provided for preparing seed mixes having a target quantity and a target ratio of different types of seeds. The process generally includes portioning quantities of different types of seeds from bulk supplies of the seeds, and combining the portioned quantities of seeds to prepare the seed mixes. The system generally includes first and second dispensing assemblies for portioning the quantities of the different types of seeds from the bulk supplies, and a mixing assembly for receiving the portioned quantities of seeds as the seed mixes. The combined quantities of the different types of seeds in the seed mixes are substantially equal to the target quantity, and a ratio of the quantities of
(Continued)

the different types of seeds is substantially equal to the target ratio.

19 Claims, 13 Drawing Sheets

Related U.S. Application Data

(60) Provisional application No. 61/321,027, filed on Apr. 5, 2010, provisional application No. 61/175,038, filed on May 3, 2009.

(51) Int. Cl.
*B28C 5/00* (2006.01)
*C12N 15/82* (2006.01)
*C04B 38/00* (2006.01)
*B28C 7/04* (2006.01)

(52) U.S. Cl.
CPC .............. *A23V 2002/00* (2013.01); *B28C 5/00* (2013.01); *B28C 7/04* (2013.01); *C04B 38/00* (2013.01); *C12N 15/8286* (2013.01); *Y10T 137/0329* (2015.04); *Y10T 137/87571* (2015.04)

(58) Field of Classification Search
CPC ........... A01C 7/20; A01C 7/046; A01C 7/081; A01C 7/102; A01C 7/105; A01C 7/124; A01C 7/128; A01C 15/00; A01C 17/00; A01C 21/00; A01C 21/005; C12N 15/8286; B28C 5/00; B28C 5/003; B28C 7/04; B28C 7/0404; B28C 7/0413; A23G 9/28; E03B 1/00; B01F 5/00; B07C 5/00; A01B 49/06; A01B 79/005
USPC .............. 800/298; 137/3, 602; 111/177, 186, 111/200; 141/9; 209/552, 592
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,339,456 A | 7/1982 | Rushing | |
| 4,372,080 A | 2/1983 | Rushing | |
| 4,383,391 A | 5/1983 | Thomas et al. | |
| 4,465,017 A | 8/1984 | Simmons | |
| 4,483,625 A | 11/1984 | Fisher | |
| 4,634,587 A | 1/1987 | Hsiao | |
| 4,735,015 A | 4/1988 | Schmolka | |
| 4,759,945 A | 7/1988 | Nemecek et al. | |
| 4,766,203 A | 8/1988 | Krieg et al. | |
| 4,797,279 A | 1/1989 | Karamata et al. | |
| 4,910,016 A | 3/1990 | Gaertner et al. | |
| 5,034,404 A | 7/1991 | Uneme et al. | |
| 5,080,925 A | 1/1992 | Kouno | |
| 5,107,787 A | 4/1992 | Kouno | |
| 5,245,040 A | 9/1993 | Maienfisch et al. | |
| 5,300,127 A | 4/1994 | Williams | |
| 5,328,942 A | 7/1994 | Akhtar et al. | |
| 5,389,399 A | 2/1995 | Bazin et al. | |
| 5,554,445 A | 9/1996 | Struszczyk et al. | |
| 5,580,544 A | 12/1996 | Dao et al. | |
| 5,622,003 A | 4/1997 | Narayanan | |
| 5,633,375 A | 5/1997 | Uneme et al. | |
| 5,661,103 A | 8/1997 | Harms et al. | |
| 5,667,298 A * | 9/1997 | Musil .................... | B28C 5/2018 366/17 |
| 5,696,144 A | 12/1997 | Royalty et al. | |
| 5,753,507 A | 5/1998 | Ohta et al. | |
| 5,791,084 A | 8/1998 | Kohno et al. | |
| 5,834,447 A | 11/1998 | Phillion et al. | |
| 5,849,320 A | 12/1998 | Turnblad et al. | |
| 5,852,012 A | 12/1998 | Maienfisch et al. | |
| 5,876,739 A | 3/1999 | Turnblad et al. | |
| 5,877,012 A | 3/1999 | Estruch et al. | |
| 5,882,713 A | 3/1999 | Eskins et al. | |
| 5,891,246 A | 4/1999 | Lund | |
| 5,918,413 A | 7/1999 | Otani et al. | |
| 5,939,356 A | 8/1999 | Wellinghoff | |
| 5,952,358 A | 9/1999 | Meunier et al. | |
| 6,023,013 A | 2/2000 | English et al. | |
| 6,060,594 A | 5/2000 | English et al. | |
| 6,063,597 A | 5/2000 | English et al. | |
| 6,186,194 B1 | 2/2001 | Poupon | |
| 6,541,448 B2 | 4/2003 | Isaac et al. | |
| 6,551,962 B1 | 4/2003 | Pershing et al. | |
| 7,202,434 B2 | 4/2007 | Lofqvist et al. | |
| 7,214,788 B2 | 5/2007 | Guzov et al. | |
| 7,417,203 B2 | 8/2008 | Lofquist et al. | |
| 9,980,423 B2 | 5/2018 | Davis et al. | |
| 2003/0186813 A1 | 10/2003 | Pershing et al. | |
| 2004/0040060 A1 | 2/2004 | Clair | |
| 2005/0042316 A1 | 2/2005 | Gregg et al. | |
| 2008/0265141 A1* | 10/2008 | Leuenberger .......... | A01C 7/105 250/216 |
| 2010/0179196 A1 | 7/2010 | Pershing et al. | |

FOREIGN PATENT DOCUMENTS

| | | |
|---|---|---|
| GB | 2 411 563 A | 9/2005 |
| WO | WO 98/13498 | 4/1998 |
| WO | WO 98/27218 | 6/1998 |
| WO | WO 99/31248 | 6/1999 |
| WO | WO 99/35913 | 7/1999 |
| WO | WO 00/66742 | 11/2000 |
| WO | WO 01/49834 A2 | 7/2001 |
| WO | WO 2006/107293 A1 | 10/2006 |
| WO | WO 2010/129410 A1 | 11/2010 |
| WO | WO 2012/078555 A1 | 6/2012 |

OTHER PUBLICATIONS

C.S. Leggatt, A New Seed Mixer and Sampler, Scientific Agriculture, vol. XXI, No. 5, Jan. 1941 (Year: 1941).*
Ariel Castro, Cultivar Mixtures, The Plant Health Instructor. DOI: 10.1094/PHI-A-2001-1230-01, updated 2007, uploaded from https://www.apsnet.org/edcenter/disimpactmngmnt/topc/cultivarmixes/Pages/default.aspx (Year: 2001).*
Agi, A. L., J. S. Mahaffey, J. R. Bradley, and J. W. Van Duyn. 2001. Efficacy of seed mixes of transgenic B.t and nontransgenic cotton against bollworm. J. Cotton Sci. 5(2): 74-80.
Agrios, In: Plant Pathology, 3$^{rd}$ Ed., Academic Press, Table of Contents, 1988 (10 pages).
Ariel Castro, 2001. Cultivar Mixtures, The Plant Health Instructor. http://www.apsnet.org/edcenter/advanced/topics/cultivarmixes/Pages/default.aspx.
Armstrong et al., Crop Science, Cell Biology & Molecular Genetics, 35(2):550-557, 1995.
Bates et al., Nature Biotechnology, Insect resistance management in GM crops: past, present and future, 23:57-62, 2005.
Bruce Tabashnik, Delaying insect adaptation to transgenic plants: seed mixtures and refugia reconsidered, Proc. R. Soc. Lond. B (1994), 255, 7-12.
C. W. Leggatt, A New Seed Mixer and Sampler, Scientific Agriculture, vol. XXI, No. 5, Jan. 1941.
C.C. Mundt, Use of Multiline Cultivars and Cultivar Mixtures for Disease Management, Annu. Rev. Phytopathol. 2002. 40:381-410.
Fehr, In: Breeding Methods for Cultivar Development, Wilcox (Ed.), American Society of Agronomy, Madison, WI, 1987 pp. 249-293.
Goatley et a., Seeded Bermudagrass Cultivar Blending Trial, 2005, www.sroseed.com /resources/pdf/articles/BlendingSeededBermudagrassVarieties.pdf.
Hills and Peters, J. Econ. Entomol., A Method of Evaluating Postplanting Insecticide Treatments for Control of Western Corn Rootworm Larvae, 64:764-765, 1971.

(56) References Cited

OTHER PUBLICATIONS

Hofte and Whitely, Microbiological Reviews, Insecticidal Crystal Proteins of Bacillus thuringiensis, 53:242-255, 1989.

Jansens et al., Crop Science, Transgenic Corn Expressing a Cry9C Insecticidal Protein from Bacillus thuringiensis Protected from European Corn Borer Damage, 37(5):1616-1624, 1997.

Lacefield et al., UK Cooperative Extension Service, University of Kentucky—College of Agriculture, Annual Ryegrass. 2003, http://www2.ca.uky.edu/agc/pubs/agr/agr179/agr179.pdf.

Li et al., Crop Protection, J., Effects of Bt cotton expressing Cry1Ac and Cry2Ab and non-Bt cotton on behavior, survival and development of Trichoplusia ni (Lepidoptera: Noctuidae), 25:940-948, 2006.

Mallet and Porter, Proc. R. Soc. Lond. B., Preventing insect adaptation to insect-resistant crops: are seed mixtures or refugia the best strategy?, 250:165-169, 1992.

Metcalf, In: Destructive and Useful Insects, Agricultural Sci. Pub. McGraw Hill Higher Education, $4^{th}$ Rev. Ed., Table of Contents, 1 page, 1962.

"Mixing Seed" Morris Fams, uploaded Feb. 27, 2012, http://www.youtube.com/watch?v=YtdDbks7OYw.

Moellenbeck et al., Nat. Biotechnol., Insecticidal proteins from Bacillus thuringiensis protect corn from corn rootworms, 19:668-672, 2001.

Ramachandran et al., Agron. J., Integrated Pest Management, Intraspecific Competition of an Insect-Resistant Transgenic Canola in Seed Mixtures, 92:368-374, 2000.

Tabashnik, Proc. Royal Soc. Series, Delaying insect adaptation to transgenic plants: seed mixtures and refugia reconsidered, 5:7-12, 1994.

Technical Note USDA —Natural Resources Conservation Service Boise, Idaho; Bozeman, Montana, TN Plant Materials No. 7, Mixing Seed With Rice Hulls, Oct. 2012.

Vaughn et al., Crop Sci., A Method of Controlling Corn Rootworm Feeding Using a Bacillus thuringiensis Protein Expressed in Transgenic Maize, 45:931-938, 2005.

Zhao et al., Transgenic Plants Expressing Two Bacillus thuringiensia Toxins Delay Insect Resistance Evolution, Nature Biotechnology, vol. 21, No. 12, Dec. 2003.

U.S. Appl. No. 13/318,592 (now U.S. Pat. No. 9,980,423 issuing May 29, 2018), filed Jan. 27, 2012, Davis et al.

* cited by examiner

SYSTEMS AND PROCESSES FOR COMBINING DIFFERENT TYPES OF SEEDS

CROSS-REFERENCE TO RELATED APPLICATIONS

This application is a divisional of U.S. patent application Ser. No. 13/318,592 filed on Jan. 27, 2012, which is a U.S. national stage filing under 35 U.S.C. § 371 of International Application No. PCT/US2010/033132 filed on Apr. 30, 2010, which claims the benefit of and priority to U.S. Provisional Application No. 61/175,038 filed on May 3, 2009, and U.S. Provisional Application No. 61/321,027 filed on Apr. 5, 2010. The entire disclosures of each of the above applications are incorporated herein by reference.

FIELD

The present disclosure relates generally to combining different types of seeds, and more particularly to preparing seed mixes having target quantities of different types of seed and target ratios of the different types of seeds.

BACKGROUND

This section provides background information related to the present disclosure which is not necessarily prior art.

Seeds are often sold in sacks which contents are typically determined by the number of seeds in the sack. For example, sacks may include around 80,000 total seeds. Often, two different types of seeds are included in the sacks. This may include harvesting the two different types of seeds into separate containers, and then unloading the seeds from the containers into batches of mixed seeds in a desired volumetric ratio. The batches of mixed seeds can then be used to prepare the sacks of seeds. However, the desired volumetric ratio of seeds in the batch does not necessarily carry through to the individual sacks of seeds prepared from the batch.

SUMMARY

This section provides a general summary of the disclosure, and is not a comprehensive disclosure of its full scope or all of its features.

Example embodiments of the present disclosure generally relate to processes for preparing seed mixes having target quantities and target ratios of different types of seeds. In one example embodiment, a process generally includes portioning a quantity of a first type of seed from a bulk supply of the first type of seed, portioning a quantity of a second type of seed from a bulk supply of the second type of seed, and combining the portioned quantities of the first and second types of seeds to prepare the seed mix. The combined quantities of the first and second types of seeds in the seed mix are substantially equal to the target quantity, and a ratio of the quantity of the first type of seed to the quantity of the second type of seed is substantially equal to the target ratio.

Example embodiments of the present disclosure generally relate to systems for preparing seed mixes having target quantities and target ratios of different types of seeds. In one example embodiment, a system generally includes a first dispensing assembly configured to portion a quantity of a first type of seed from a bulk supply of the first type of seed, a second dispensing assembly configured to portion a quantity of a second type of seed from a bulk supply of the second type of seed, and a mixing assembly configured to receive the portioned quantities of the first and second types of seeds as a seed mix. The combined quantities of the first and second types of seeds in the seed mix are substantially equal to the target quantity, and a ratio of the quantity of the first type of seed to the quantity of the second type of seed is substantially equal to the target ratio.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
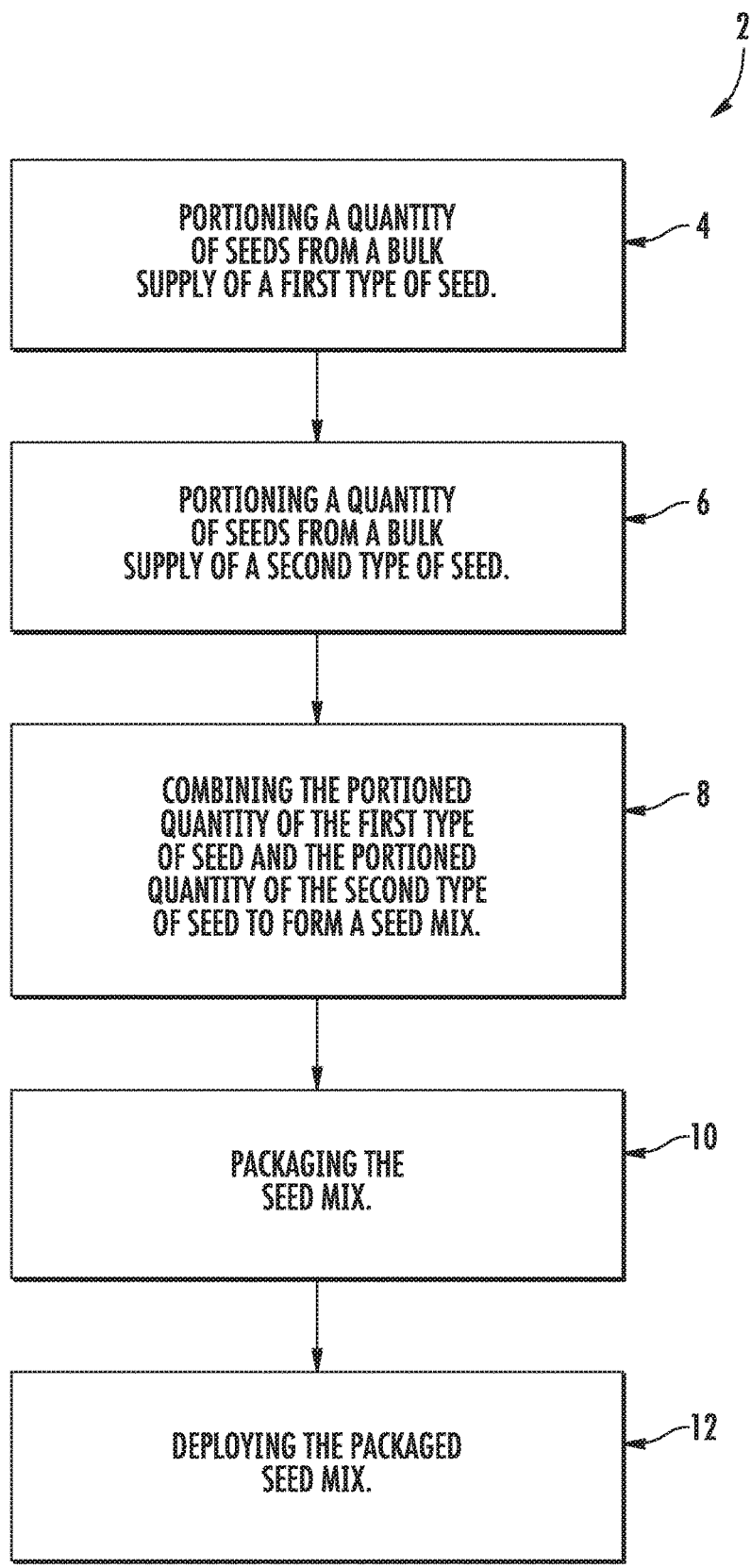
FIG. 1 illustrates an example process for preparing seed mixes having a target quantity and a target ratio of different types of seeds.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference now to the drawings, FIG. 1 illustrates an example embodiment of a process, generally at reference number 2, for preparing a seed mix from two different types of seeds (e.g., for use as part of a seed mix strategy, etc.). The example process 2 may be automated (e.g., having at least one or more totally automated operation, having at least one or more semi-automated operation, etc.) or manual within the scope of the present disclosure. In addition, the process 2 may be used for preparing a seed mix from more than two different types of seeds within the scope of the present disclosure.

The different types of seeds used in preparing the seed mix may include any desired types of seeds within the scope of the present disclosure. For example, the seeds may include corn seed, cotton seed, canola seed, soybean seed, or rice seed, etc. Also for example, the seeds may include transgenic seeds having one or more transgenes; seeds having two or more different transgenes; seeds having two or more different transgenes each conferring a pest resistance to the same pest but by different modes of action; seeds having two or more different transgenes each conferring a pest resistance to different pests; seeds having stacks of different configured to provide stacked transgenic events; seeds having two or more stacks of different transgenes; seeds having transgenes encoding proteins with insecticidal properties, pesticidal properties, etc.; seeds having transgenes conferring pest resistance to one or more of *Ostrinia nubilalis, Diatraea graandiosella, Diabrotica barben, Diabrotica virgifera virgifera, Richia albicosta, Agrotis ipsilion, Spodoptera frugiperda, Helicoverpa zea*, etc.; seeds treated with pesticidal agents, fungicidal agents, herbicidal agents, fertilizer agents, biocontrol agents, etc.; non-transgenic seeds; combinations of such seeds; etc.

For example, in the illustrated embodiment a first type of seed (e.g., a major component of the seed mix, etc.) may include transgenic seeds. The transgenic seeds may have one or more properties or expressions such as herbicidal tolerance, dicamba resistance, corn rootworm resistance (including resistance to various species of rootworm), cornborer resistance (including resistance to various species of cornborer), corn earworm resistance, cotton bollworm resistance, pink bollworm resistance, fall armyworm resistance, other pest resistance, etc. And, a second type of seed (e.g., a minor component of the seed mix, etc.) may include refuge seeds.

The refuge seeds may be transgenic or they may be non-transgenic. The refuge seeds may include seeds having different properties or expressions than the transgenic seeds, or less than all of the properties or expressions of the transgenic seeds (e.g., less than all of the pesticide properties or expressions, etc.). The refuge seeds may still include, however, properties or expressions such as insecticidal tolerance, herbicidal tolerance, fungicidal tolerance, etc. within the scope of the present disclosure. For example, the refuge seeds may include seeds of one or more plant varieties that can be grown into plants that act as a refuge for pests that would typically feed on plates grown from the transgenic seeds, but for genetic modification of the transgenic seeds to resist such pests. In addition, the refuge seeds may be uniform in nature, in that they are comprised of seeds from a single variety of plant, or they may be non-uniform in nature and comprise seeds from two or more varieties of plant. Further, the refuge seeds may be provided that are particularly attractive to a given crop pest, at least relative to other plants grown from the seed mix (e.g., from the transgenic seeds, etc.). For example, the refuge seeds may be selected based on expected color, timing of silks or flowering, plant health, vigour, etc. to be nutritionally attractive to certain pests, and/or they may comprise one or more transgene that results in the production of pest attractants.

As shown in FIG. 1, the example process 2 generally includes portioning (e.g., weighing, counting, measuring, etc.) a predetermined quantity of seeds from a bulk supply of the first type of seed (as indicated generally at reference number 4), and portioning a predetermined quantity of seeds from a bulk supply of the second type of seed (as indicated generally at reference number 6). The example process 2 then includes combining the portioned quantities of the first and second types of seeds (as indicated generally at reference number 8) to form the seed mix. The first and second types of seeds are generally mixed, blended, etc. together as they are combined (e.g., via gravity, via mechanical operations, etc.) to help generally uniformly distribute the seeds in the seed mix. The first and second types of seeds can be combined in suitable containers within the scope of the present disclosure.

The predetermined quantities of the first and second types of seeds to be added to the seed mix are selected based on a target quantity of total seeds to be included in the seed mix and a target ratio of the first type of seed to the second type of seed to be achieved in the seed mix. Thus, when prepared, the seed mix will have a total quantity of seeds substantially equal to the target quantity of total seeds, and a ratio of the first type of seed to the second type of seed substantially equal to the target ratio.

The target quantity of first and second types of seeds to be included in the seed mix may include any discrete quantity of seeds, between about a hundred seeds and about a hundred million seeds, or any other desired quantity within the scope of the present disclosure. The target quantity of seeds may include a quantity of seeds suitable for reception within a particular type of packaging, size of packaging, etc. Further, the target quantity of seeds may be based on use for the seed mix, demand for the seed mix, crop size, field size, equipment compatibility, equipment capacity, transport requirements, other factors considered in determining seed capacities, etc. For example, the target quantity of seeds may be about 80,000 seeds, as generally associated with a commercial bag of seed; about 4 million seeds, as generally associated with a commercial SeedPak™ container; or any other desired quantity of seeds.

The target ratio of the first type of seed to the second type of seed to be achieved in the seed mix may include any desired ratio within the scope of the present disclosure. For example, the seed mix may include about nineteen parts of the first type of seed and about one part of the second type of seed. As such, a ratio of the first type of seed to the second type of seed in the seed mix is about 19:1 (i.e., the seed mix comprises about 95% of the first type of seed and about 5% of the second type of seed). As such, about 95% of the resulting crop will be yielded from the first type of seed and about 5% of the resulting crop will be yielded from the second type of seed. Alternatively, seed mixes may have ratios of first types of seeds to second types of seeds of about 1:1, about 2:1, about 3:1, about 4:1, about 9:1, about 10:1, about 20:1, about 49:1, about 50:1, about 99:1, ratios therebetween, etc. within the scope of the present disclosure. Further, seed mixes may have ratios of the first types of seeds to the second types of seeds based on acceptable ranges of ratios (e.g., within a given tolerance, etc.), such as a range of about 22:1 to about 15:1, etc. within the scope of the present disclosure.

The target ratio of the first and second types of seeds in the seed mix may be selected to provide crops (planted from packages containing the seed mix) having certain desired percentages of plants grown from the first and second types of seeds. For example, the target ratio may be selected based on a desired seed mix strategy, based on a desired IRM program, etc. A seed mix package of such first and second types of seeds may include a percentage of refuge seeds and a percentage of transgenic seeds, thus eliminating issues of enforcement and compliance with regulatory standards for recombinant crops and block refuge requirements.

The first and/or second types of seeds used in preparing the seed mix according to the example process 2 may include seeds having substantially uniform sizes (e.g., AF, AF2, AR, AR2, P22, ARPM, etc.), shapes, and/or colors within industry recognized tolerances. As such, the bulk supplies of the first and/or second types of seeds used to prepare the seed mix in the example process 2 may include seeds each having substantially the same size, shape, and/or color. While not required, providing a seed mix in which the first and second types of seeds each have the same size, shape, and/or color may help ensure that the particular seed mix is planted, and may help inhibit subsequent removal of, for example, the second type of seed (e.g., the refuge seed type, etc.) from the seed mix by end users (e.g., in an attempt by the end users to only use the first type of seed (i.e., the transgenic seed type), etc.).

The bulk supplies of the first and second types of seeds may be provided in any acceptable number of different quantities known in the art, for example, for providing multiple seeds to automated seed blending systems, etc. In some example embodiments, bulk supplies of seeds may include packages of seeds (e.g., bags of seeds, SeedPak™ containers, etc.), outputs of seeds from other processing systems, bulk stores of seeds in bins or containers, etc.

In the example process 2, portioning a predetermined quantity of the first and second types of seeds includes portioning a desired (or target) weight of the first and second types of seeds from their bulk supplies into a receiving container. The desired weight of the seeds may include, for example, a predetermined weight based on the particular size of the seed (e.g., AF2, etc.), a predetermined weight based on the particular type of seed, etc. And, the desired weight may be associated with, or indicative of, a particular number/quantity of the first and second types of seeds (e.g., based on an average density of the first and second types of seeds in their respective bulk supplies, etc.) to be included in the seed mix. In other example embodiments, processes for preparing seed mixes may include portioning desired volumes of different types of seeds to receiving containers (where the desired volumes are associated with, or indicative of, a particular number of seeds). In still other example embodiments, processes for preparing seed mixes may include counting desired quantities of different types of seeds and then delivering the counted quantities to receiving containers to prepare the seed mixes.

Table 1 illustrates example correlations/conversions between seed weight and seed quantity for various different size combinations of first and second types of seeds for use in achieving a seed mix having a target quantity of seeds of about 80,000 and a target ratio of the first type of seed to the second type of seed of about 19:1. Such correlations/conversions can be prepared as necessary for desired seeds and used in the example process 2. For a seed mix requiring the first and second seed types to each have seed sizes of AR, a weight of about 46.8 pounds of the first type of seed would be portioned from the bulk supply of the first type of seed and delivered to the receiving container and a weight of about 2.2 pounds of the second type of seed would portioned from the bulk supply of the second type of seed and delivered to the receiving container to thereby prepare the seed mix.

TABLE 1

| First Type of Seed | | | | Second Type of Seed | | | |
| --- | --- | --- | --- | --- | --- | --- | --- |
| Size | Quantity by Weight | Target Weight (lbs) | Quantity | Size | Quantity by Weight | Target Weight (lbs) | Quantity |
| AF2 | 1756 | 42.6 | 74806 | AF2 | 1709 | 2.4 | 4102 |
| AR2 | 1566 | 48.6 | 76108 | AF2 | 1709 | 2.4 | 4102 |
| AF2 | 1756 | 42.7 | 74981 | AR2 | 1462 | 2.8 | 4094 |
| AR2 | 1566 | 48.7 | 76264 | AR2 | 1462 | 2.8 | 4094 |
| AR | 1622 | 46.8 | 75910 | AR | 1843 | 2.2 | 4055 |
| AF | 1730 | 44.9 | 77677 | AR | 1843 | 2.1 | 3870 |
| P22 | 1904 | 40.8 | 77683 | AR | 1843 | 2.2 | 4055 |
| AR | 1622 | 46.9 | 76072 | AF | 1929 | 2.1 | 4051 |
| AF | 1730 | 44.9 | 77677 | AF | 1929 | 2.1 | 4051 |
| P22 | 1904 | 40.9 | 77874 | AF | 1929 | 2.1 | 4051 |
| AF | 1730 | 44.5 | 76985 | P22 | 2830 | 1.5 | 4245 |
| AR | 1622 | 46.5 | 75423 | P22 | 2830 | 1.5 | 4245 |
| AF2 | 1756 | 40.2 | 70591 | AF2 | 1709 | 4.8 | 8203 |
| ARPM | 1622 | 47.3 | 76721 | ARPH | 1827 | 2.2 | 4019 |

With continued reference to FIG. 1, the example process 2 also includes packaging the seed mix (as indicated generally at reference number 10) in packages for subsequent storage, distribution, etc. The first and second types of seeds are distributed throughout the packages generally uniformly (following the combining operation 8). However, additional mixing, blending, etc. operations, however, may be provided (e.g., after packaging the seed mix) to further help distribute the first and second types of seeds throughout the packages as necessary. The packages may include any suitable packages within the scope of the present disclosure including, for example, bags, boxes, jugs, single packages, single packages as part of SeedPak™ containers, etc. As can be seen, the particular weight (and thus number) of seeds delivered to each package is determined and generally known (on a package-by-package basis). As such, the example process 2 can repeatedly provide packages of seeds having desired quantities and ratios of seeds.

The example process 2 further includes deploying the packaged seed mix as desired (as indicated generally at reference number 12). This can include, for example, transporting the seed mix (in the packages) to end users (e.g., farmers, etc.) for planting in fields. The packages can provide for efficient and/or effective transport of the seed mix to the end users and/or for planting of the seed mix in the fields (e.g., for distribution to planting equipment, etc.).

While not shown in FIG. 1, the example process 2 may also include additional operations directed toward at least one or more of sizing seeds, conditioning seeds, treating seeds, and quality testing of seeds within the scope of the present disclosure. For example, the first and/or second types of seeds may be processed prior to bulking in the bulk supplies so as to have the substantially uniform sizes (e.g., AF2, etc.), shapes, and/or colors within industry recognized tolerances (e.g., such that the seeds are not distinguishable, or are not distinguishable as they are planted, etc.). The seeds may also be processed in such a way, for instance by application of a seed coating, as to make them indistinguishable or distinguishable as they are planted. The seed may further be processed, for instance, by coating or pelleting to allow for more convenient use by planting machinery, or to provide a fungicide or insecticide component to the planted material, such as by a seed coating.

In other example embodiments, processes for preparing seed mixes may include combining portioned quantities of first, second, and third types of seeds. Target quantities of seeds in these seed mixes are inclusive of the portioned quantities of the first, second, and third types of seeds. Here, the third type of seed may include at least one property or expression not included in the first or second types of seeds. In one of the example embodiments, the target quantity of the first, second, and third types of seeds in the seed mix is about 80,000 total seeds. And, a target ratio of the first type of seed to the second type of seed to the third type of seed in the seed mix is about 8:1:1, such that the seed mix includes about 80% of the first type of seed, about 10% of the second type of seed, and about 10% of the third type of seed.

In still other example embodiments, processes for preparing seed mixes may include combining portioned quantities of first, second, and third types of seeds where the second types of seeds in the seed mixes include refuge seed types to be included in the seed mixes at predetermined percentages (e.g., about 1% to about 25%, about 5% to about 10%, etc.) such that the same quantities of the second types of seeds are included in the seed mixes regardless of the quantities, percentages, etc. of the first and third types of seeds, etc. The remainder of the total quantities of seeds in the seed mixes is then made up of the first and second types of seeds, combined at various percentages and/or ratios. In one of the example embodiments, the second type of seed is to be included in the seed mix at a predetermined percentage of about 5%. And, the first and third types of seeds are to be included in the seed mix at equal percentages of about 47.5%. Here, a target ratio of the first type of seed to the second type of seed to the third type of seed is about 9.5:1:9.5. In another one of the example embodiments, the second type of seed is to be included in the seed mix at a predetermined percentage of about 5%. And, the first and third types of seeds are to be included in the seed mix at respective percentages of about 20% and abut 75%. Here, a target ratio of the first type of seed to the second type of seed to the third type of seed is about 4:1:15.

In still other example embodiments, processes for preparing seed mixes may include combining portioned quantities of more than three different types of seeds.

Figure 2:
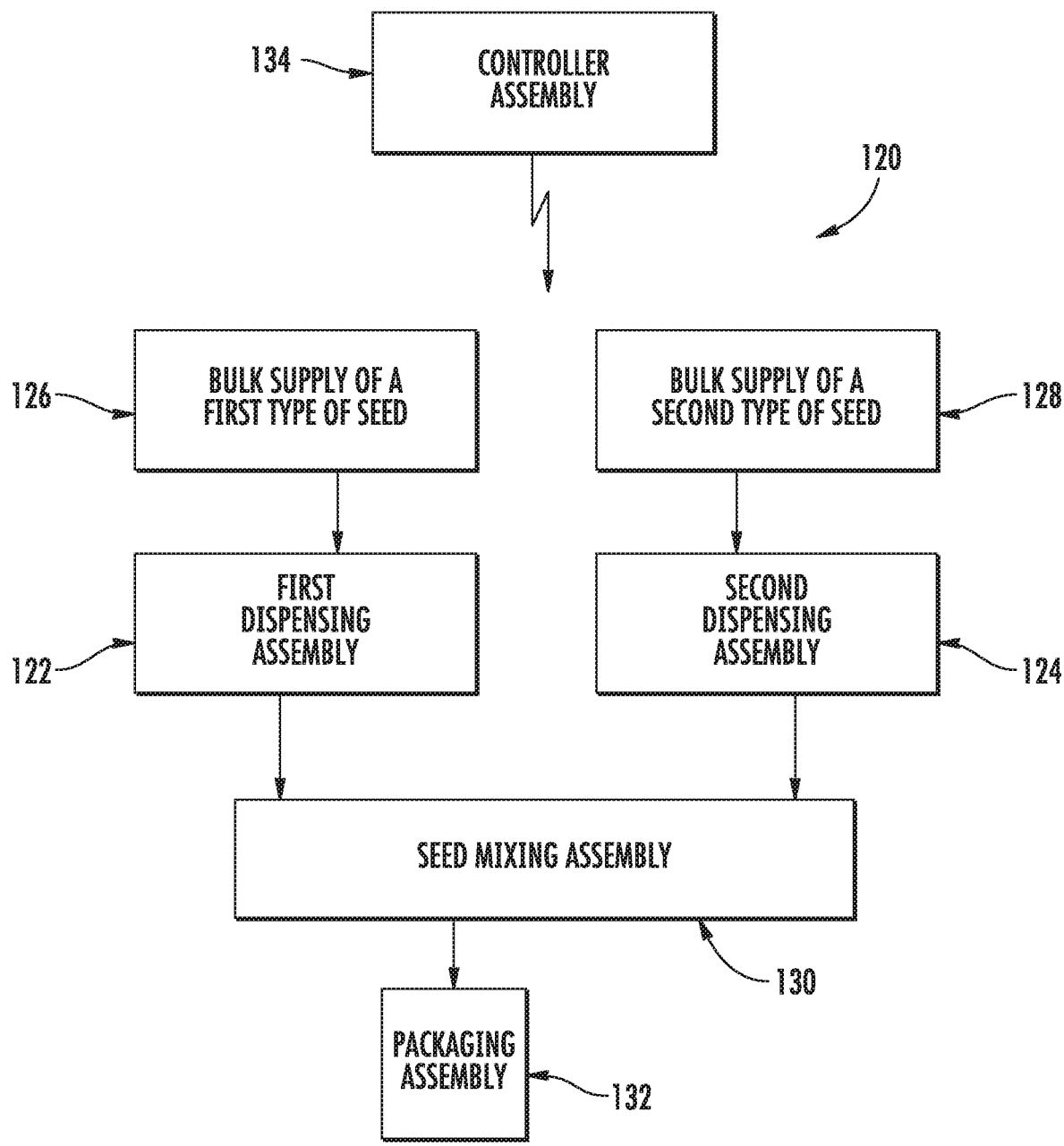
FIG. 2 is a block diagram of an example embodiment of a seed blending system configured for use in preparing seed mixes having a target quantity and a target ratio of different types of seeds.

FIG. 2 schematically illustrates an example embodiment of a seed blending system 120 configured for use in preparing a seed mix from two different types of seeds. The system 120 is configured to repeatedly prepare seed mixes that each have a desired target quantity of first and second types of seeds and a desired target ratio of the first type of seed to the second type of seed. The illustrated system 120 may be used in accordance with the process 2 previously described.

The illustrated system 120 generally includes a first dispensing assembly 122 and a second dispensing assembly 124. The first dispensing assembly 122 is configured to portion (e.g., weigh, count, measure volumes, etc.) a predetermined quantity of seeds from a bulk supply 126 of a first type of seed. And, the second dispensing assembly 124 is configured to portion (e.g., weigh, count, measure volumes, etc.) a predetermined quantity of seeds from a bulk supply 128 of a second type of seed. Any suitable dispensing assembly may be used for portioning quantities of the first and second types of seeds (and subsequently delivering the seeds from the dispensing assembly as desired) within the scope of the present disclosure.

The illustrated system 120 also includes a seed mixing assembly 130 configured to receive and blend, mix, etc. the first and second types of seeds to form the seed mix. Blending the first and second types of seeds together may be achieved passively (e.g., through gravity, etc.) as the seeds are received in the seed mixing assembly 130. For example, the seeds may generally blend uniformly together as they are received together in the seed mixing assembly 130. Blending the first and second types of seeds may also include active blending, mixing, etc. operations to help generally uniformly distribute the seeds in the seed mix. Any suitable seed mixing assembly may be used within the scope of the present disclosure.

The illustrated system 120 further includes a packaging assembly 132 configured to receive the seed mix from the seed mixing assembly 130 into a package. This operation may further help uniformly blend the first and second types of seeds together. Thus, when the seed mix is received in the package, the first and second seeds are generally uniformly mixed. And, a total quantity of the first and second types of seeds in the package is generally equal to the target quantity, and a ratio of the first type of seed to the second type of seed in the package is generally equal to the target ratio. Moreover, each package produced by the system 120 includes substantially the target quantity of total seeds and the target ratio of the first type of seed to the second type of seed. Any suitable packaging assembly may be used within the scope of the present disclosure.

Operation of the illustrated system 120 may be controlled by a controller assembly 134 (e.g., a remote controller assembly, a hardwired controller assembly, etc.). The controller assembly 134 may include one or more personal computers, laptops, workstations, servers, PDAs, other processing devices, etc. known in the art for providing control signals to various components of the automated system 120 (e.g., the first dispensing assembly 122, the second dispensing assembly 124, the seed mixing assembly 130, the packaging assembly 132, etc.). The controller assembly 134 may be programmed by a user at the outset of a production run to direct the system 120 in the packaging of seed mixes. For example, the controller assembly 134 may receive various inputs from the user such as sizes of seeds being handled, target ratios between first and second types of seeds, target quantities of seeds to be included in packages, known weight correlations between seed sizes and seed quantities, quantities of first and/or second types of seeds to be portioned, etc. The controller assembly 134 may then utilize the inputs received from the user to provide control signals to the various assemblies of the system 120 to prepare desired seed mixes (e.g., seed mixes having target quantities of different types of seeds and/or desired ratios of the different types of seeds, etc.). In other example embodiments, various different types of information may be supplied to controller assemblies to ensure that dispensing assemblies portion appropriate quantities of seeds to provide target quantities of seeds having ratios equal to predetermined values.

FIGS. 3-6 illustrate an example embodiment of another automated seed blending system 220 including one or more aspects of the present disclosure. The illustrated system 220 is configured (e.g., sized, shaped, constructed, etc.) for use in repeatedly preparing seed mixes that each have a target quantity of first and second types of seeds, and that each have a target ratio of the first type of seed to the second type of seed. In the illustrated embodiment, the first type of seed (e.g., the major component of the seed mixes, etc.) includes transgenic seeds, and the second type of seed (e.g., the minor component of the seed mixes, etc.) includes refuge seeds. And, the seed mixes prepared by the system 220 are intended to be packaged in bags, each substantially including a target quantity of seeds of about 80,000 total seeds and a target ratio of the first type of seed to the second type of seed of about 19:1 (i.e., about 95 percent of the first type of seed and about 5 percent of the second type of seed). The illustrated system 220 may be used in accordance with the process 2 previously described.

Figure 3:
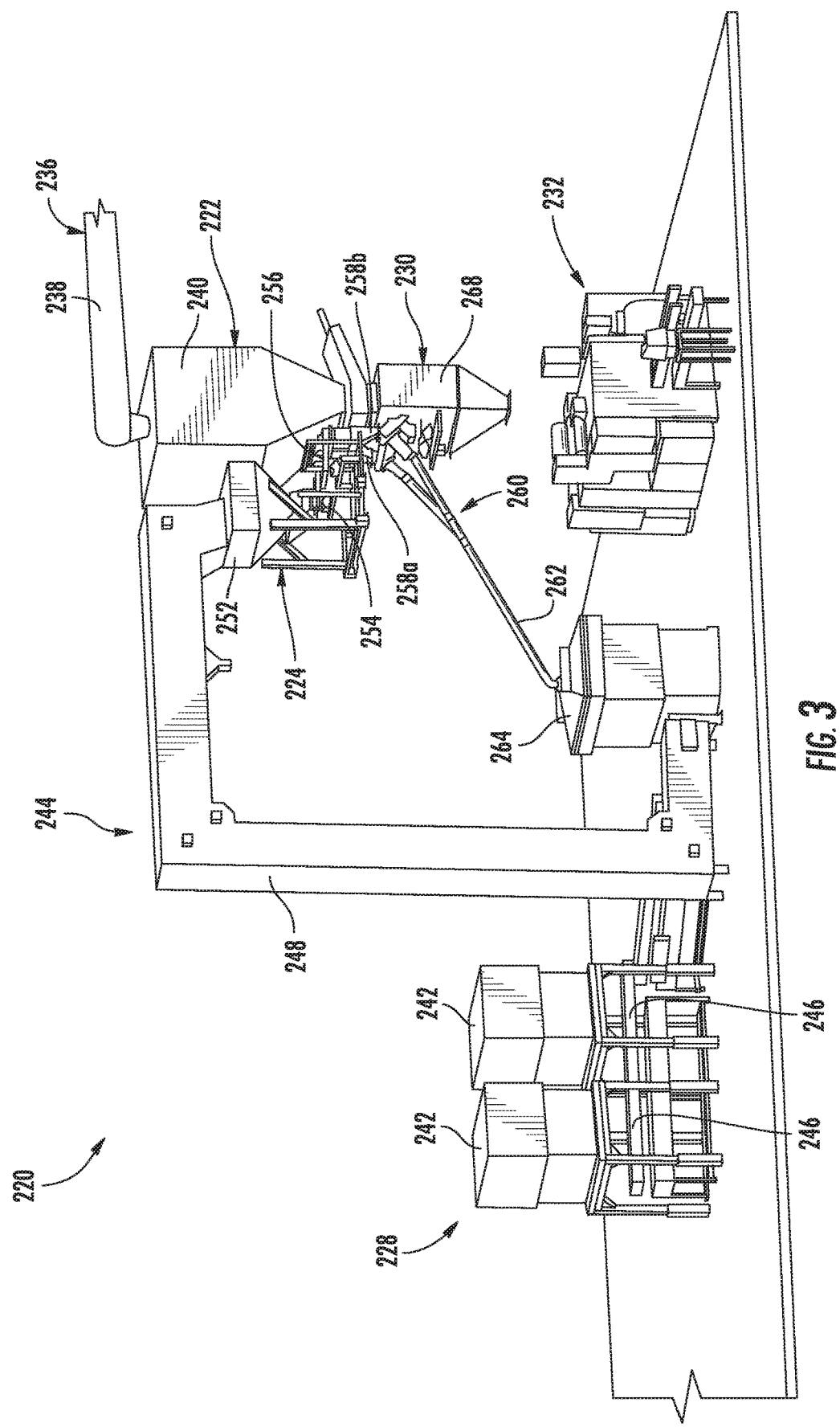
FIG. 3 is a perspective view of an example embodiment of a seed blending system configured for use in preparing seed mixes having a target quantity and a target ratio of different types of seeds, and for packaging the seed mixes in bags.
Figure 4:
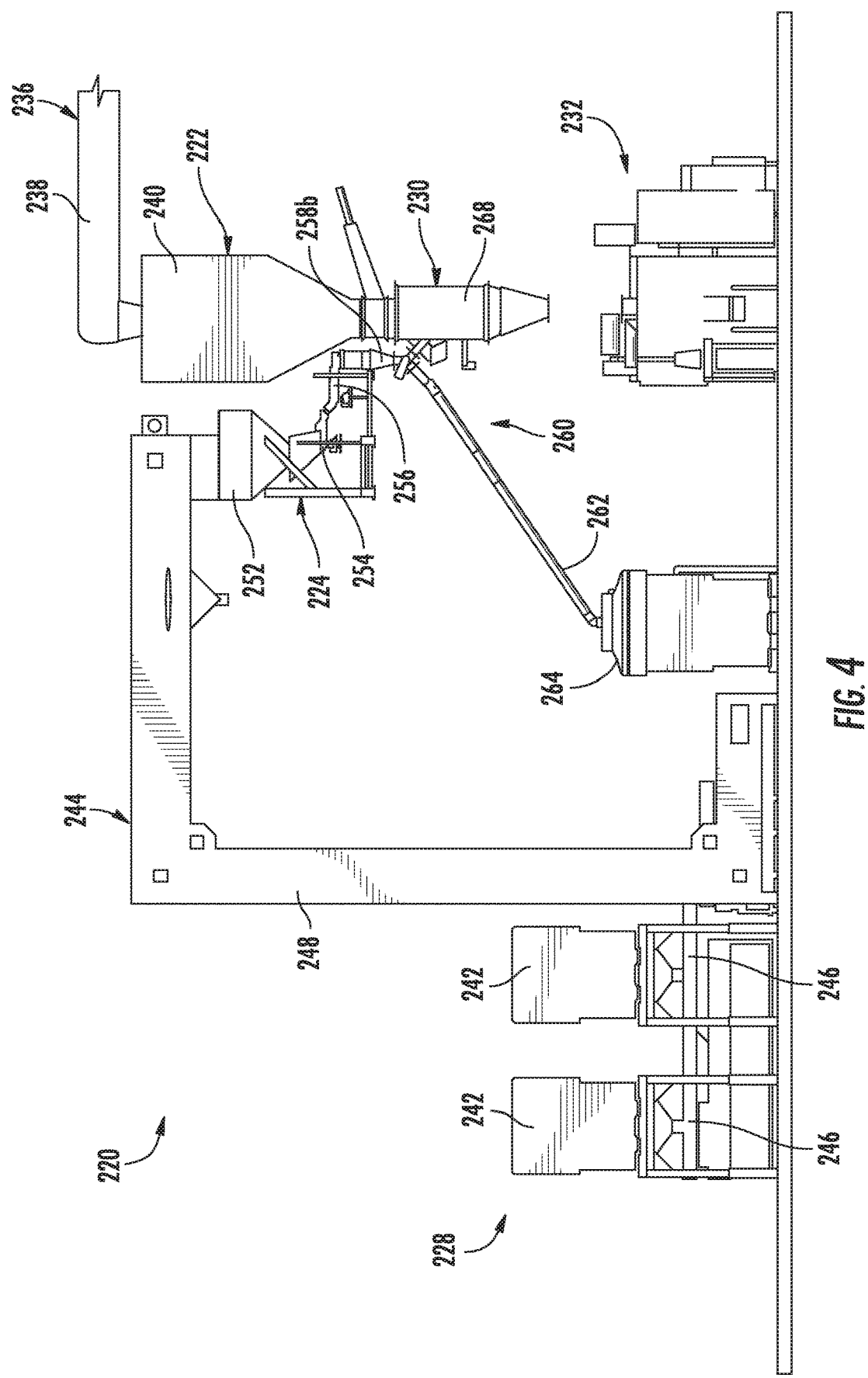
FIG. 4 is a front elevation view of the seed blending system of FIG. 3.

As shown in FIGS. 3 and 4, the illustrated system 220 generally includes first and second dispensing assemblies 222 and 224, a seed mixing assembly 230, and a packaging assembly 232 located generally below the seed mixing assembly 230. The first dispensing assembly 222 is configured to deliver, in repeated operations, a portioned quantity of the first type of seed to the seed mixing assembly 230. And, the second dispensing assembly 224 is configured to deliver, in repeated operations, a portioned quantity of the second type of seed to the seed mixing assembly 230. The seed mixing assembly 230 then operates to blend (e.g., passively, actively, etc.) the first and second types of seeds, and deliver the combined first and second types of seeds (as seed mixes) to the packaging assembly 232 for preparation for subsequent distribution. The seed packaging assembly 232 may include any suitable seed packaging assembly within the scope of the present disclosure, for example, suitable for packaging seed mixes in desired containers (e.g., bags, etc.).

The first type of seed is provided to the first dispensing assembly 222 from a bulk supply (not shown) of the first type of seed. A first transport 236 is configured to convey the first type of seed from the bulk supply to the first dispensing assembly 222. In the illustrated embodiment, the first transport 236 includes a pipe 238, and the first type of seed is gravity conveyed through the pipe 238, as desired, to the first dispensing assembly 222. In other example embodiments, systems may include, for example, conveyors, buckets, other types of transports, etc. for transporting seeds from bulk supplies of first types of seeds to first dispensing assemblies.

The first dispensing assembly 222 includes a housing 240 supporting therein a surge bin (not shown), generally known in the art, for initially receiving and holding a temporary amount of the first type of seed from the first transport 236. The first dispensing assembly 222 operates to deliver desired quantities of the first type of seed from the temporary amount held in the surge bin to the seed mixing assembly 230. And, the first transport 236 operates to refill the surge bin with the first type of seed as necessary (to maintain the temporary amount of the first type of seed held therein). As such, a supply of the first type of seed is generally always readily available in the surge bin for delivery to the seed mixing assembly 230.

In an example operation of the first dispensing assembly 222 (which is generally known in the art), a first gate (not shown) operates to selectively release (via gravity) the first type of seed from the surge bin to a vibratory feeder (not shown) located within the housing 240 generally below the surge bin. A second gate (not shown) then operates to selectively release (via gravity) the first type of seed from the vibratory feeder to first and second hoppers (not shown) located within the housing and generally below the vibratory feeder. As an example, the vibratory feeder may initially operate to fill the first hopper with seeds. Then, as the first hopper delivers a desired quantity of the seeds to the seed mixing assembly 230, the vibratory feeder may operate to fill the second hopper with seeds. And then, as the second hopper delivers a desired quantity of the seeds to the seed mixing assembly 230, the vibratory feeder may again operate to fill the first hopper with seeds. This sequential use of the first and second hoppers (which may span, for example, about 4-6 seconds, etc.) can reduce wait time for preparing the seed mixes. And, this operation may continue as desired, for example, until a desired number of seed mixes are prepared, etc. In other example embodiments, systems may include first dispensing assemblies having a number of hoppers other than two (e.g., three, etc.).

The hoppers of the first dispensing assembly 222 are each configured to receive and hold a suitable amount of the first type of seed necessary, for example, to prepare individual ones of the desired seed mixes. In the illustrated embodiment, for example, the first and second hoppers are each configured to hold at least about 76,000 seeds, i.e., at least about 95 percent of the 80,000 total seeds to be included in each of the seed mixes (so that a ratio of the first type of seed to the second type of seed in each of the prepared seed mixes is about 19:1). In other example embodiments, systems may include first dispensing assemblies having hoppers configured to hold more than or less than about 76,000 seeds, for example, depending on target quantities of seeds to be included in seed mixes prepared by the systems, or depending on target ratios of various types of seeds to be included in seed mixes prepared by the systems, etc.

With continued reference to FIGS. 3 and 4, the second type of seed is provided to the second dispensing assembly 224 of the system 220 from a bulk supply 228 of the second type of seed. In the illustrated embodiment, the bulk supply 228 of the second type of seed is included in first and second containers 242. The containers 242 allow for easy refilling, replacing, etc. of the second type of seed during operation to maintain the supply of the second type of seed as desired. The containers 242 may also allow for easy changing of the second type of seed, for example, from one type of refuge seed to another type of refuge seed, etc. A second transport 244 is configured to convey the second type of seed from the containers 242 to the second dispensing assembly 224. Seed conduits 246 extend from each of the containers 242 to the second transport 244. The second type of seed is conveyed, as desired, from the seed conduits 246 (e.g., through a frame housing 248 of the second transport 244, etc.) to the second dispensing assembly 224. In other example embodiments, systems may include, for example, conveyors, buckets, other types of transports, etc. for transporting seeds from bulk supplies of second types of seeds to second dispensing assemblies.

The second dispensing assembly 224 includes a surge bin 252, generally known in the art, for initially receiving and holding a temporary amount (e.g., about twenty-two cubic feet, etc.) of the second type of seed from the second transport 244. The second dispensing assembly 224 operates to deliver desired quantities of the second type of seed from the temporary amount held in the surge bin 252 to the seed mixing assembly 230. And, the second transport 244 operates to refill the surge bin 252 with the second type of seed as necessary (to maintain the temporary amount of the second type of seed held in the surge bin 252). As such, a supply of the second type of seed is generally always readily available in the surge bin 252 for delivery to the seed mixing assembly 230.

In an example operation of the second dispensing assembly 224, a first gate (not shown) operates to selectively release (via gravity) the second type of seed from the surge bin 252 to a vibratory feeder 254 located generally below the surge bin 252. A second gate (not shown) then operates to selectively release (via gravity) the second type of seed from the vibratory feeder 254 to a weighing plate 256. The weighing plate 256 is associated with a load cell (not shown) for monitoring and/or measuring weight of the second type of seed received on the weighing plate 256. The weighing plate 256 collects the second type of seed released from the vibratory feeder 254 and, once a desired weight of the second type of seed is achieved (i.e., a preprogrammed weight associated with about 4,000 seeds of the second type of seed in the illustrated embodiment (e.g., within acceptable tolerances, etc.)), directs the second type of seed (e.g., via gravity and selective operation of a gate, etc.) to first and second hoppers 258a and 258b located adjacent the weighing plate 256. As an example, the weighing plate 256 may initially operate to fill the first hopper 258a with weighed seeds, and then immediately receive and weigh additional seeds from the vibratory feeder 254. As the first hopper 258a delivers the seeds to the seed mixing assembly 230, the weighing plate 256 may operate to fill the second hopper 258b with weighed seeds. The weighing plate 256 may then again immediately receive and weigh additional seeds from the vibratory feeder 254. And then, as the second hopper 258b delivers the seeds to the seed mixing assembly 230, the weighing plate 256 may again operate to fill the first hopper 258a with weighed seeds. This sequential use of the first and second hoppers 258a and 258b can reduce wait time for preparing the seed mixes. And, this operation may continue as desired, for example, until a desired number of seed mixes are prepared, etc. In other example embodiments, systems may include second dispensing assemblies having a number of hoppers other than two (e.g., three, etc.). In other example embodiments, individual scales may be associated with each of the first and second hoppers 258a and 258b for weighing seeds received from surge bin 252 and delivering the weighed seeds to the respective hoppers 258a and 258b (e.g., instead of or in addition to the weighing plate 256, etc.).

The hoppers 258a and 258b of the second dispensing assembly 224 are each configured to receive and hold a suitable amount of the second type of seed necessary, for example, to prepare individual ones of the desired seed mixes. In the illustrated embodiment, for example, the first and second hoppers 258a and 258b are each configured to hold at least about 4,000 seeds, i.e., at least about 5 percent of the 80,000 total seeds to be included in each of the seed mixes (so that a ratio of the first type of seed to the second type of seed in each of the prepared seed mixes is about 19:1). In other example embodiments, systems may include second dispensing assemblies having hoppers configured to hold more than or less than about 4,000 seeds, for example, depending on target quantities of seeds to be included in seed mixes prepared by the systems, or depending on target ratios of various types of seeds to be included in seed mixes prepared by the systems, etc.

The second dispensing assembly 224 also includes a return 260 coupled to lower portions of the first and second hoppers 258a and 258b. The return 260 is included in the system 220, for example, as part of quality control of seeds being added to the seed mixes. For example, the return 260 can operate to empty un-wanted quantities of seed from the first and second hoppers 258a and 258b based on analysis (e.g., visual analysis, etc.) of the seeds along the second transport 244, at the second dispensing assembly 224, etc. The return 260 can also operate to empty misfed quantities of seeds received in the first and second hoppers 258a and 258b from the second transport 244, etc. The illustrated return 260 includes pipes 262 extending from each of the first and second hoppers 258a and 258b to a bin 264. The pipes 262 transport, as desired (e.g., via operation of a gate, a valve, etc.), the quantities of seed to be emptied from the hoppers 258a and 258b to the bin 264 for subsequent recycling into the system 220 (e.g., for return to the bulk supply 228 of the second type of seed, etc.), for storage, for disposal, etc. In other example embodiments, systems may include first dispensing assemblies having returns as part of quality control of first types of seeds being added to seed mixes prepared by the systems.

Figure 5:
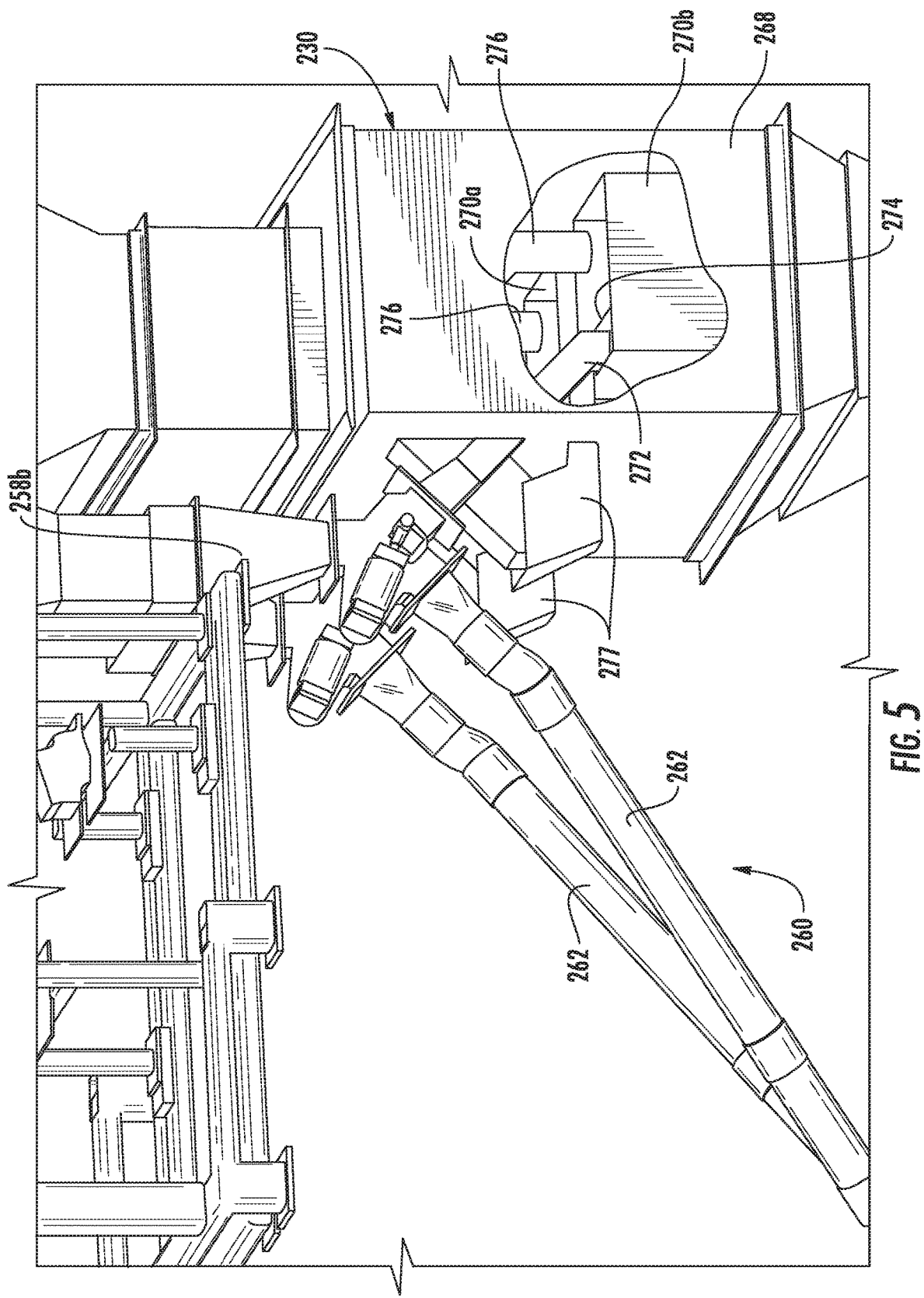
FIG. 5 is an enlarged perspective view of a seed mixing assembly of the seed blending system of FIG. 3 with part of a housing of the seed mixing assembly broken away to see internal weigh buckets thereof.
Figure 6:
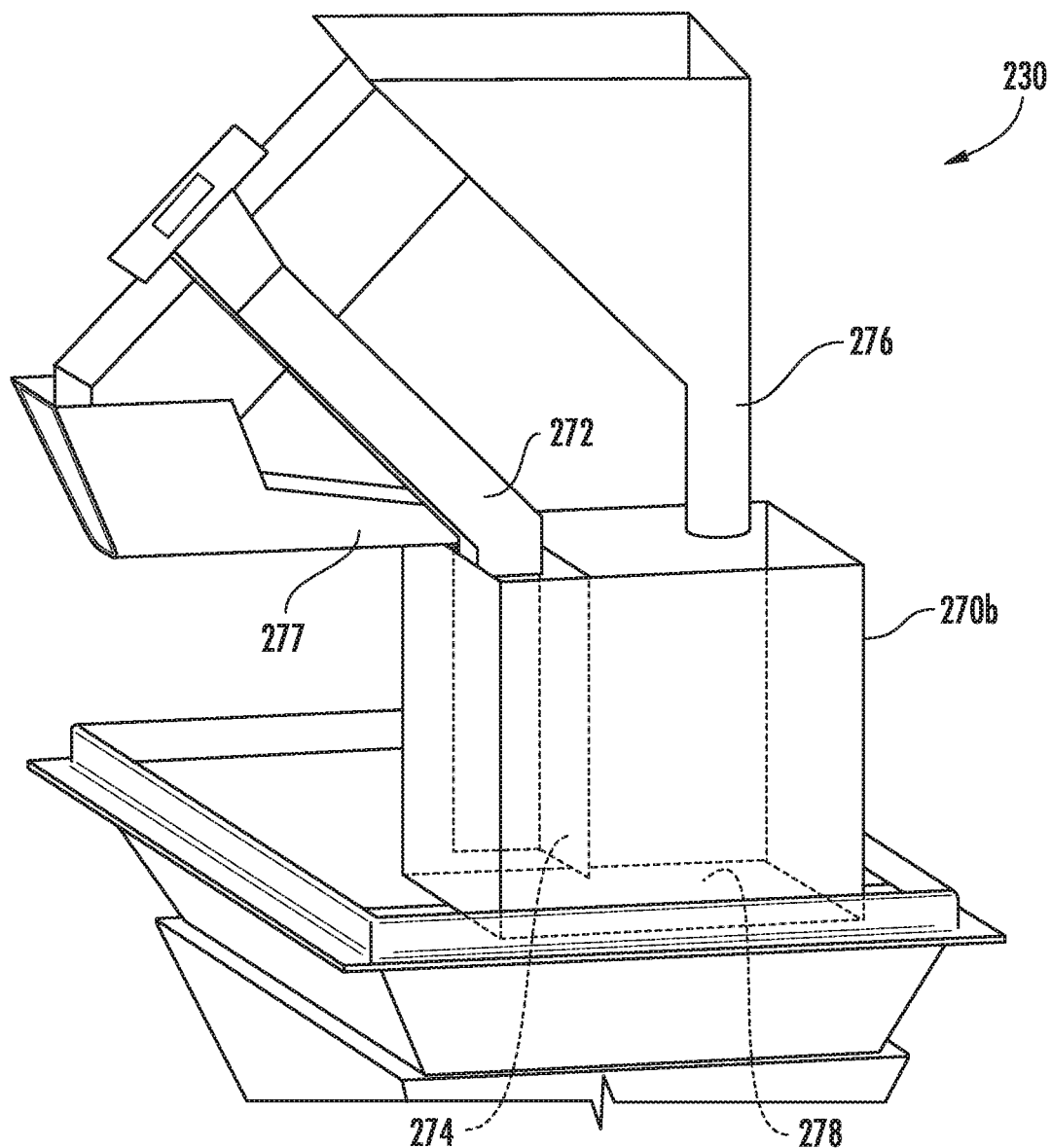
FIG. 6 is an enlarged perspective view of a weigh bucket of the seed mixing assembly of FIG. 5.

With additional reference now to FIGS. 5 and 6, the seed mixing assembly 230 includes a housing 268, and first and second weigh buckets 270a and 270b supported within the housing 268. The weigh buckets 270a and 270b are each configured to receive the first and second types of seeds from the respective first and second dispensing assemblies 222 and 224. When the weigh buckets 270a and 270b are filled with desired quantities of both the first and second types of seeds, the weigh buckets 270a and 270b operate to release (via gravity) the combined seeds to the packaging assembly 232 for further processing. In the illustrated embodiment, the first and second weigh buckets 270a and 270b are associated with load cells (not shown) for monitoring and/or measuring weight of the weigh buckets 270a and 270b (and the combined weight of the first and second types of seeds received therein). The load cells allow the system 220 to accurately prepare, in repeated operations, seed mixes in the weigh buckets 270a and 270b having desired weights of the first and second types of seeds. Thus, seed mixes having desired quantities (e.g., target quantities, etc.) of the first and second types of seeds and desired ratios (e.g., target ratios, etc.) thereof can be repeatedly delivered to the packaging assembly 232. As can be seen, the particular weight (and thus number) of seeds delivered to each package via the packaging assembly 232 is determined and generally known (on a package-by-package basis). As such, the example system 220 can repeatedly provide packages of seeds having desired quantities and ratios of seeds.

In an example operation of the illustrated seed mixing assembly 230, the second dispensing assembly 224 delivers a portioned quantity of the second type of seed (i.e., a desired weight of the second type of seed, as weighed by the weighing plate 256, having a known weight associated with a quantity of about 4,000 seeds) from its first hopper 258a, via a chute 272, to the first weigh bucket 270a. A guide 274 is provided to help direct the seeds from the chute 272 into the first weigh bucket 270a. The first dispensing assembly 222 delivers the first type of seed from its first hopper (via a main chute 276 and a secondary chute 277 for fine-tuned delivery) into the first weigh bucket 270a (either after the second dispensing assembly 224 begins delivering seeds, at about the same time the second dispensing assembly 224 begins delivering seeds, or before the second dispensing assembly 224 begins delivering seeds). As the first type of seed is added to the first weigh bucket 270a, it generally mixes, blends, etc. with the second type of seed in the weigh bucket 270a. At the same time, a load cell associated with the first weigh bucket 270a incrementally monitors and/or measures the additional weight of the first type of seed being added. When a desired weight of the first type of seed (i.e., a weigh associated with about 76,000 seeds (e.g., within acceptable tolerances, etc.)) is added to the first weigh bucket 270a (taking into account the known weight of the second type of seed already in the weigh bucket 270a), delivery of the first type of seed is stopped. The first weigh bucket 270a then operates to release (via gravity through a lower door 278) the combined first and second types of seeds (i.e., as a seed mix) to the packaging assembly 232 for further processing (which operation may also allow for blending of the seeds as they move from the first weigh bucket 270a to the packaging assembly 232). Operation of the seed mixing assembly 230 to fill the second weigh bucket 270b with portioned quantities of the first and second types of seeds and to then deliver the combined seeds to the packaging assembly 232 is substantially the same.

In the illustrated embodiment, the first and second weigh buckets 270a and 270b are operated generally in series (in connection with the hoppers (e.g., hoppers 258a and 258b, etc.) of the first and second dispensing assemblies 222 and 224), such that only one of the weigh buckets 270a and 270b releases seeds to the packaging assembly 232 at any one time. While the first weigh bucket 270a is releasing seeds to the packaging assembly 232 (as just described), the second weigh bucket 270b is being filled with the first and second types of seeds from the first and second dispensing assemblies 222 and 224. This provides a generally sequential, series, uniform, etc. operation of the first and second weigh buckets 270a and 270b in receiving first and second types of seeds from the first and second dispensing assemblies 222 and 224, as well as in releasing the combined seeds to the packaging assembly 232.

In other example embodiments, systems may include seed mixing assemblies configured to substantially simultaneously receive first and second types of seeds into weigh buckets at about the same time. Here, determining weights of the first type of seed to be substantially simultaneously added to the weigh buckets with the second type of seeds is accomplished by taking into account known weights of the second type of seeds being added (as measured by weigh plates of second dispensing assemblies of the systems). In still other example embodiments, systems may include seed mixing assemblies configured to receive pre-weighed quantities of both first and second types of seeds into buckets from first and second dispensing assemblies (such that a weight of the first type of seed is known and a weight of the second type of seed is known). The buckets may then also be weighed as part of a quality control procedure to confirm that the total weight is achieved. In still other example embodiments, systems may include seed mixing assemblies having a number of weigh buckets other than two (e.g., three, etc.).

Figure 7:
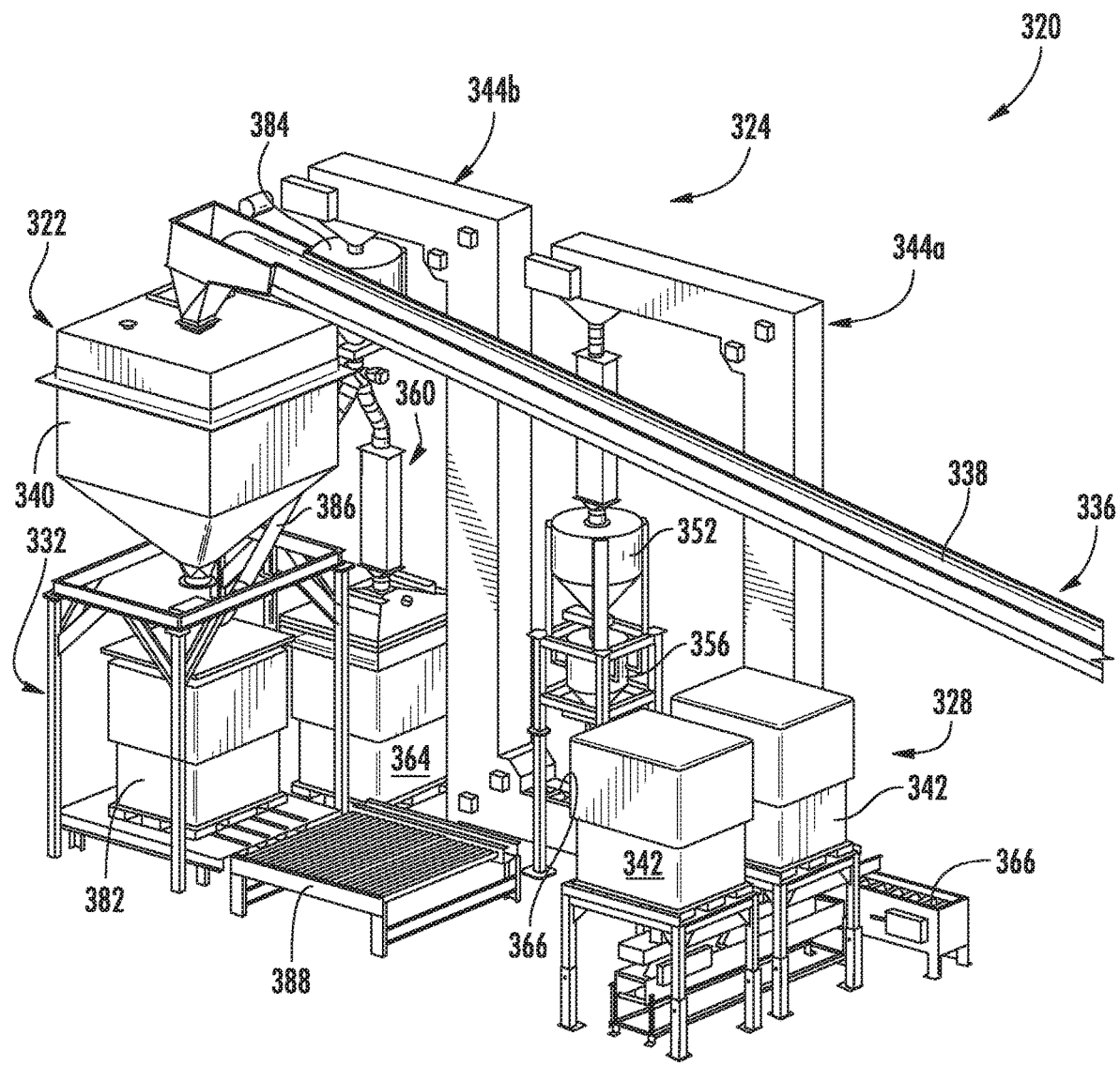
FIG. 7 is a perspective view of an example embodiment of a seed blending system configured for use in preparing seed mixes having a target quantity and a target ratio of different types of seeds, and for packaging the seed mixes in see packs.
Figure 8:
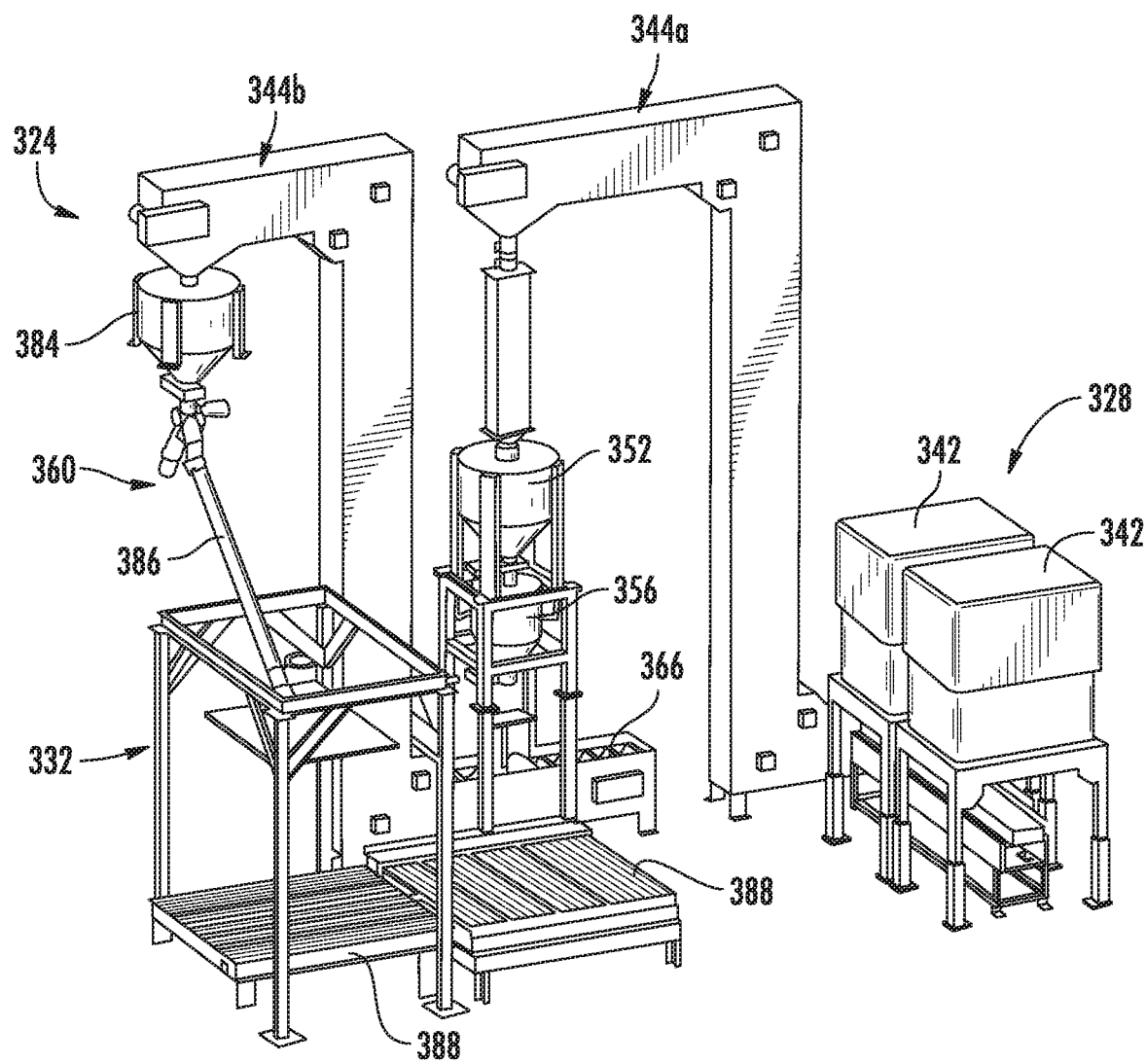
FIG. 8 is a perspective view of the seed blending system of FIG. 7 with a first dispensing assembly removed.
Figure 9:
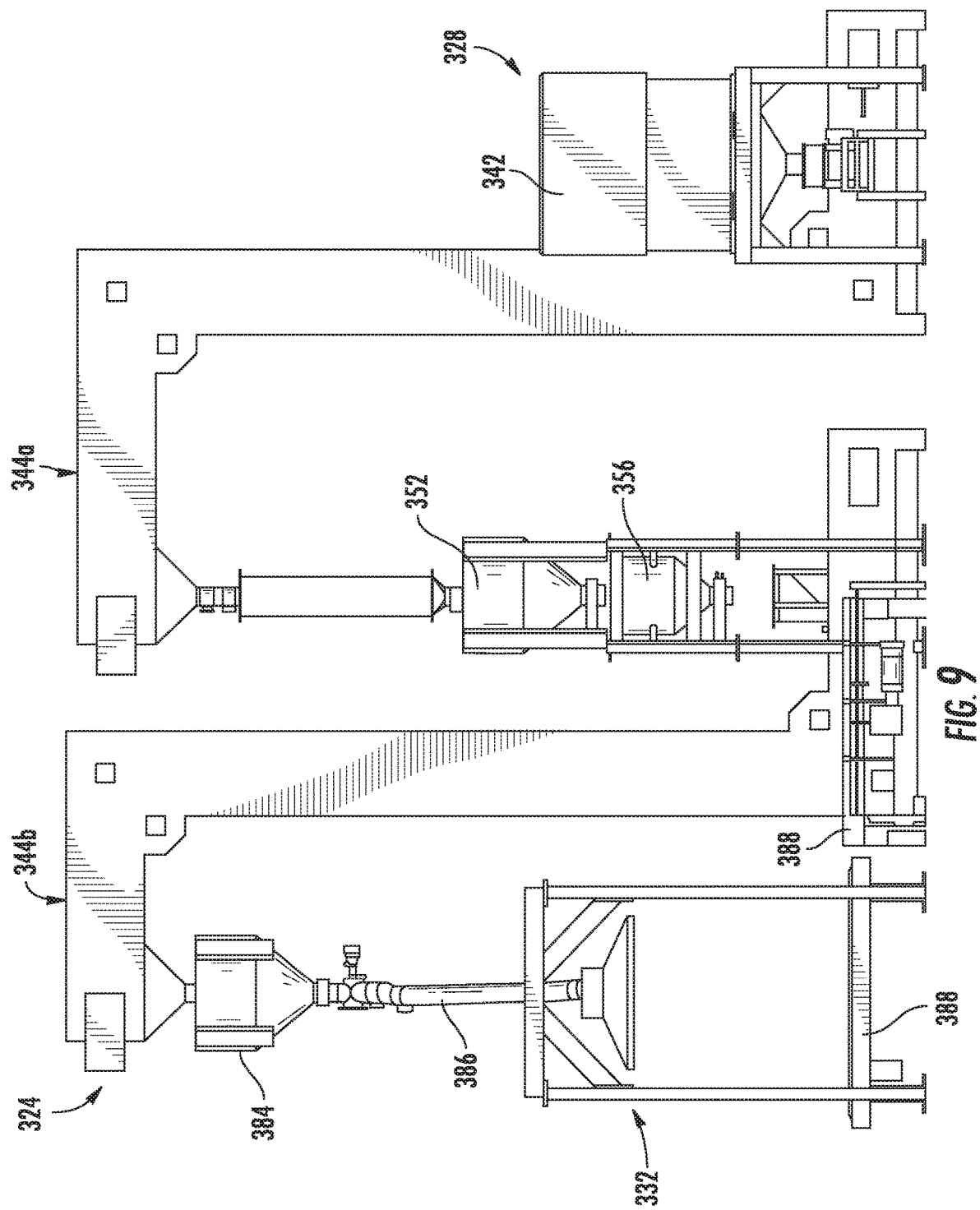
FIG. 9 is a front elevation view of the seed blending system of FIG. 8.

FIGS. 7-9 illustrate an example embodiment of another automated seed blending system 320 including one or more aspects of the present disclosure. The illustrated system is similar to the seed blending system 220 previously described and illustrated in FIGS. 3-6, but generally operates to package the seed mixes in SeedPak™ containers (e.g., SeedPak™ container 382 in FIG. 7, etc.) instead of bags. For example, the illustrated system 320 is configured (e.g., sized, shaped, constructed, etc.) for use in repeatedly preparing seed mixes that each have a target quantity of first and second types of seeds, and that each have a target ratio of the first type of seed to the second type of seed. In the illustrated embodiment, the first type of seed (e.g., the major component of the seed mixes, etc.) includes transgenic seeds, and the second type of seed (e.g., the minor component of the seed mixes, etc.) includes refuge seeds. And, the seed mixes prepared by the system 320 are intended to be packaged in SeedPak™ containers, each substantially including a target quantity of seeds of about 4,000,000 total seeds (e.g., for addition to SeedPak™ containers, etc.), and a target ratio of the first type of seed to the second type of seed of about 19:1

(i.e., about 95 percent of the first type of seed and about 5 percent of the second type of seed).

The illustrated system 320 generally includes first and second dispensing assemblies 322 and 324 and a packaging assembly 332 located generally below the first and second dispensing assemblies 322 and 324. The first dispensing assembly 322 is configured to deliver, in repeated operations, a portioned quantity of the first type of seed to SeedPak™ containers (e.g., the SeedPak™ container 382 in FIG. 7, etc.) positioned within the packaging assembly 332. And, the second dispensing assembly 324 is configured to deliver, in repeated operations, a portioned quantity of the second type of seed to the SeedPak™ containers positioned within the packaging assembly 332. The first and second types of seeds are blended together to form seed mixes as they are received in the SeedPak™ containers.

The first type of seed is provided to the first dispensing assembly 322 from a bulk supply (not shown) of the first type of seed. A first transport 336 is configured to convey the first type of seed from the bulk supply to the first dispensing assembly 322. In the illustrated embodiment, the first transport 336 includes a pipe 338, and the first type of seed is conveyed through the pipe 338, as desired, to the first dispensing assembly 322 (e.g., gravity, pneumatically, mechanically, etc.).

The first dispensing assembly 322 includes a housing 340 supporting therein a surge bin (not shown), generally known in the art, for initially receiving and holding a temporary amount of the first type of seed from the first transport 336. The first dispensing assembly 322 operates to deliver the first type of seed from the temporary amount held in the surge bin to the packaging assembly 332. And, the first transport 336 operates to refill the surge bin with the first type of seed as necessary (to maintain the temporary amount of the first type of seed held therein). As such, a supply of the first type of seed is generally always readily available in the surge bin for delivery to the packaging assembly 332.

In an example operation of the first dispensing assembly 322 (which is generally known in the art), a first gate (not shown) operates to selectively release (via gravity) the first type of seed from the surge bin to a vibratory feeder (not shown) located within the housing 340 generally below the surge bin. A second gate (not shown) then operates to selectively release (via gravity) the second type of seed from the vibratory feeder to a weighing plate (not shown). The weighing plate is associated with a load cell for monitoring and/or measuring weight of the first type of seed received on the weighing plate. The weighing plate collects the first type of seed released from the vibratory feeder and, once a desired weight of the first type of seed is achieved (i.e., a weight associated with about 3,800,000 seeds of the first type of seed in the illustrated embodiment), directs the first type of seed (e.g., via gravity and selective operation of a gate, etc.) to the packaging assembly 332 generally immediately below the first dispensing assembly 322.

The surge bin of the first dispensing assembly 322 is configured to receive and hold a suitable amount of the first type of seed necessary, for example, to prepare the desired seed mixes within the SeedPak™ containers. In the illustrated embodiment, for example, the surge bin is configured to hold at least about 3,800,000 seeds, i.e., at least about 95 percent of the 4,000,000 total seeds to be included in each of the seed mixes (so that a ratio of the first type of seed to the second type of seed in each of the prepared seed mixes is about 19:1). In other example embodiments, systems may include first dispensing assemblies having surge bins configured to hold more than or less than about 3,800,000 seeds, for example, depending on target quantities of seeds to be included in seed mixes prepared by the systems, or depending on target ratios of various types of seeds to be included in seed mixes prepared by the systems, etc.

The second type of seed is provided to the second dispensing assembly 324 of the system 320 from a bulk supply 328 of the second type of seed. In the illustrated embodiment, the bulk supply 328 of the second type of seed is included in containers 342. The containers 342 allow for easy refilling, replacing, etc. of the second type of seed during operation to maintain the supply of the second type of seed as desired. The containers 342 may also allow for easy changing of the second type of seed, for example, from one type of refuge seed to another type of refuge seed, etc.

The second dispensing assembly 324 generally includes transports 344a and 344b (having conveyors 366), a first surge bin 352, a weighing unit 356, and a second surge bin 384. The second dispensing assembly 324 operates to portion quantities of the second type of seed from the temporary amount held in the first surge bin 352 and then deliver the portioned quantities of seeds to the second surge bin 384 for subsequent addition to the SeedPak™ containers (at the packaging assembly 332). As part of this operation, the transport 344a operates to refill the first surge bin 352 with the second type of seed as necessary to maintain the temporary amount of the second type of seed held in the first surge bin 352 so that a supply of the second type of seed is generally always readily available in the first surge bin 352 for delivery to the weighing unit 356. And, the transport 344b operates to convey weighed quantities of seeds from the weighing unit 356 to the second surge bin 384 for subsequent delivery to the packaging assembly 332.

In an example operation of the second dispensing assembly 324, a first gate (not shown) operates to selectively release (via gravity) the second type of seed from the first surge bin 352 to the weighing unit 356 generally below the first surge bin 352. The weighing unit 356 is associated with a load cell (not shown) for monitoring and/or measuring weight of the second type of seed received in the weighing unit 356. The weighing unit 356 collects the second type of seed released from the first surge bin 352 and, once a desired weight of the second type of seed is achieved (i.e., a weight associated with about 200,000 seeds of the second type of seed in the illustrated embodiment), directs the second type of seed (e.g., via gravity and selective operation of a gate, etc.) to the transport 344b. The transport 344b delivers the weighed quantities of the second type of seed to the second surge bin 384 which is configured to then subsequently deliver (via a pipe 386) the quantities of the second type of seed to a SeedPak™ container (e.g., SeedPak™ container 382 in FIG. 7, etc.) positioned within the packaging assembly 332. The weighing unit 356 may continue to operate to direct weighed quantities of the second type of seed to the transport 344b for sequentially feeding to the second surge bin 384. This sequential, series operation of the second dispensing assembly 324 can then continue as desired, for example, until a desired number of seed mixes are prepared, etc.

The second dispensing assembly 324 also includes a return 360 coupled to a lower portion of the second surge bin 384. The return 360 is included in the system 320, for example, as part of quality control of seeds being added to the seed mixes. For example, the return 360 can operate to empty un-wanted quantities of seed from the second surge bin 384 based on analysis (e.g., visual analysis, etc.) of the seeds along the second transports 344a and/or 344b, at the surge bins 352 and 384, etc. The return 360 can also operate to empty misfed quantities of seeds received in the first surge bin 352 (and weighing unit 356), etc. The return 360 operates to transport, as desired (e.g., via operation of a gate, a valve, etc.), the quantities of seeds to be emptied from the second surge bin 384 to bin 364 for subsequent recycling into the system 320 (e.g., return to the bulk supply 328 of the second type of seed, etc.), for storage, for disposal, etc.

The packaging assembly 332 of the illustrated system 320 includes a floor structure 388 for sequentially moving (e.g., via rollers, etc.) SeedPak™ containers into the packaging assembly 332 for receiving portioned quantities of the first and second types of seeds from the respective first and second dispensing assemblies 322 and 324. Thus, SeedPak™ containers can be sequentially positioned generally under the first and second dispensing assemblies 322 and 324 to receive portioned quantities of the first and second types of seeds. And, each of the prepared SeedPak™ containers will contain a seed mix having desired quantities (e.g., target quantities, etc.) of the first and second types of seeds and desired ratios (e.g., target ratios, etc.) thereof. In addition, the SeedPak™ containers each receive seeds from the first and second dispensing assemblies 322 and 324 at about the same time. As such, the first and second types of seeds are generally uniformly blended, mixed, etc. together as they are delivered to the SeedPak™ containers.

Figure 10:
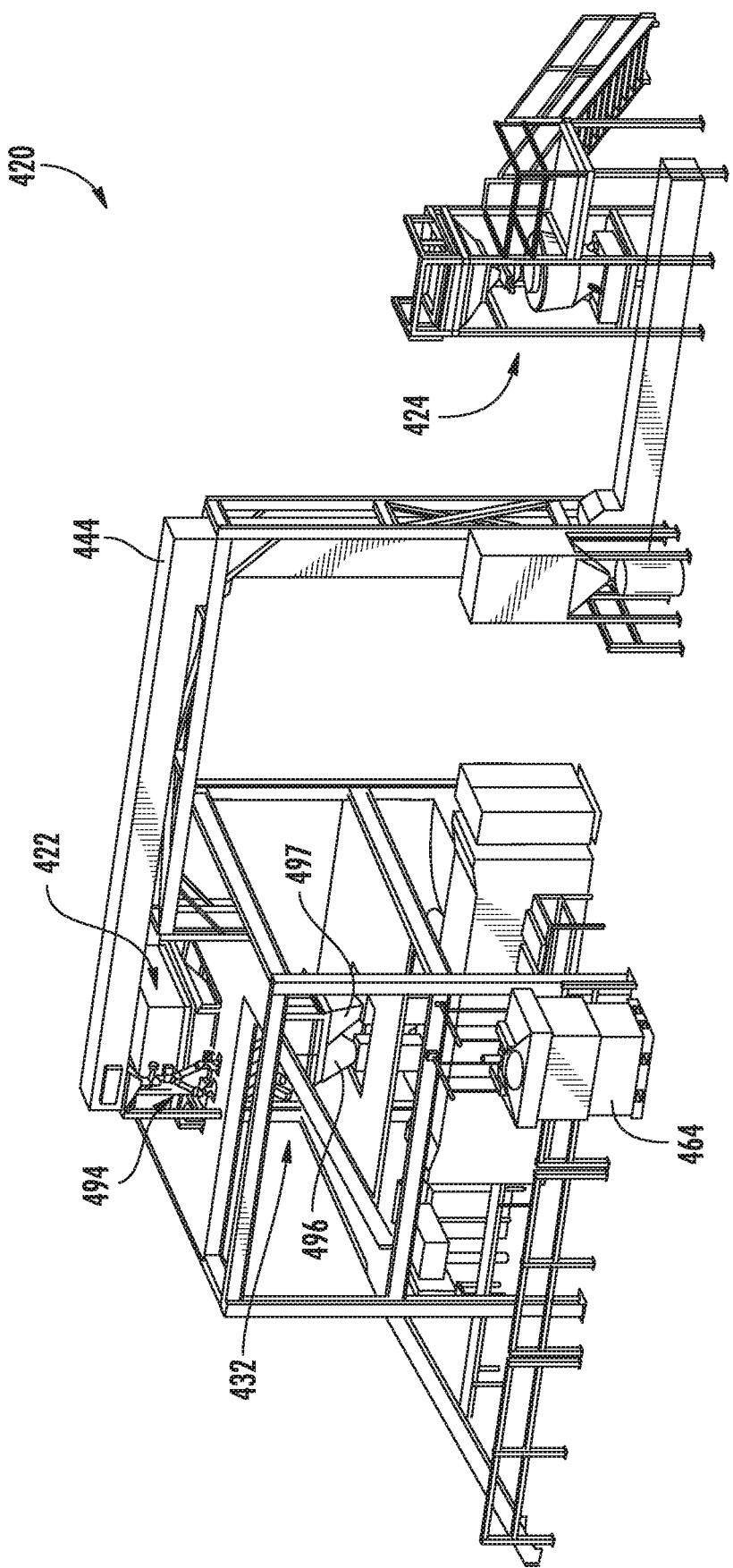
FIG. 10 is a perspective view of another example embodiment of a seed blending system configured for use in preparing seed mixes having a target quantity and a target ratio of different types of seeds, and for packaging the seed mixes in desired containers, for example, bags, SeedPak™ containers, etc.
Figure 11:
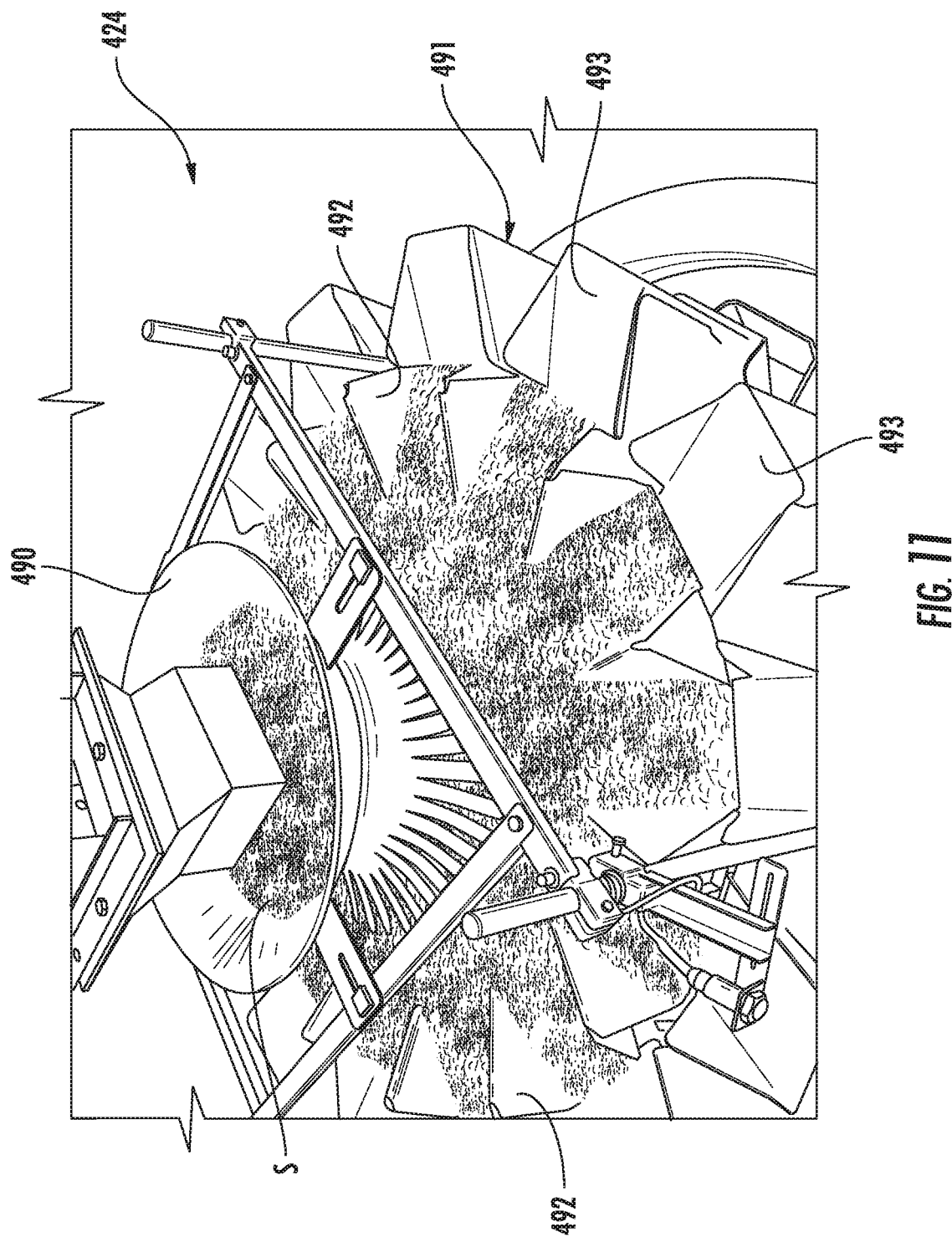
FIG. 11 is a perspective view of a second dispensing assembly of the system of FIG. 10.
Figure 12:
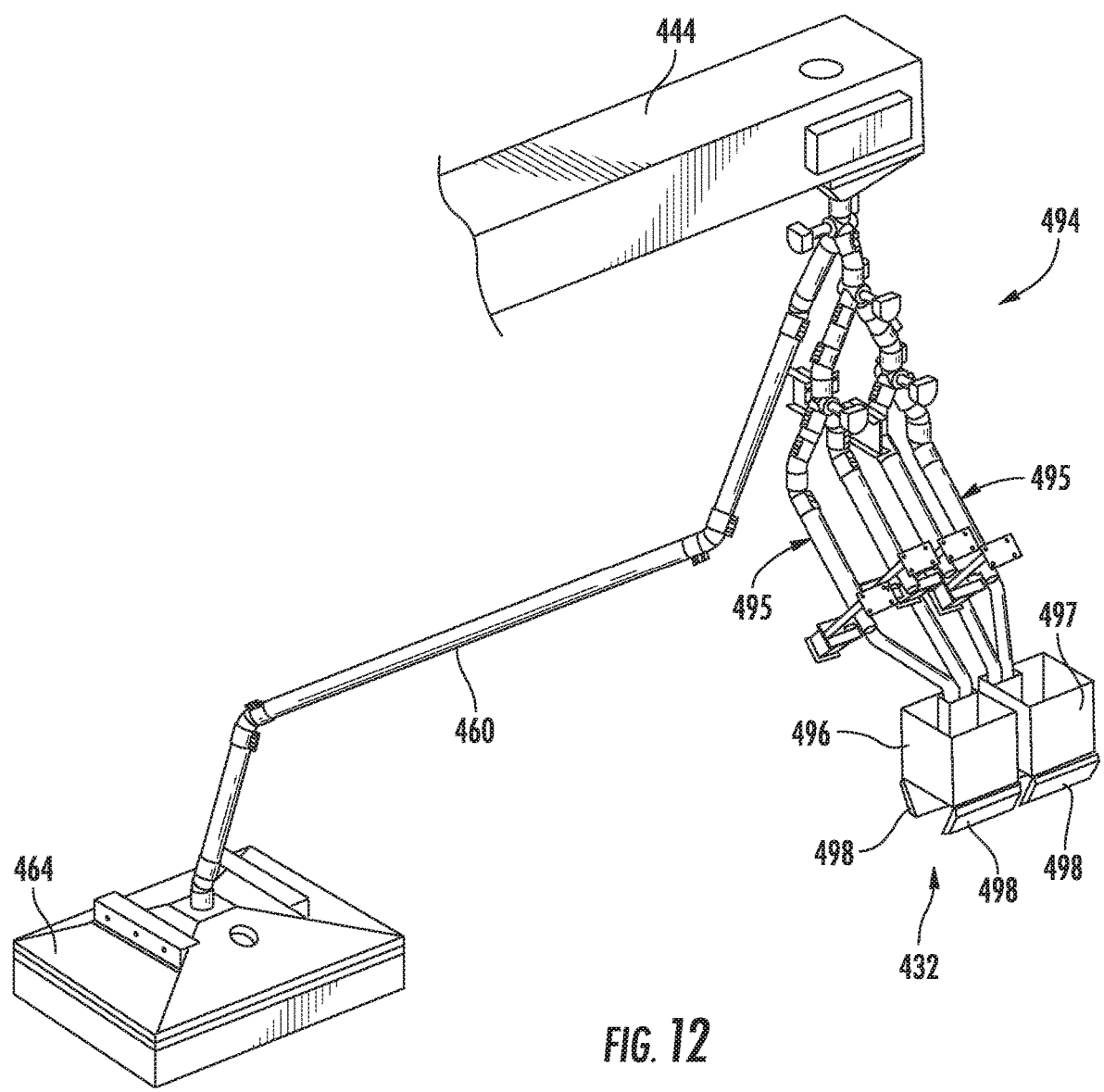
FIG. 12 is a perspective view of part of a delivery sub-assembly of the system of FIG. 10.

FIGS. 10-12 illustrate an example embodiment of another system 420 including one or more aspects of the present disclosure. The system 420 is configured for use in preparing seed mixes having target quantities of different types of seeds. The illustrated system 420 is automated and is operable to combine portioned quantities of a first type of seed (e.g., a transgenic seed, etc.) from a bulk supply 426 of the first type of seed and portioned quantities of a second type of seed (e.g., a refuge seed, etc.) from a bulk supply 428 of the second type of seed.

As shown in FIG. 10, the bulk supply 426 of the first type of seed is disposed and configured to provide, deliver, etc. the first type of seed (e.g., which may have been processed so as to have a substantially uniform size, within industry recognized tolerances, etc.) to a first dispensing assembly 422. The first dispensing assembly 422 is configured to portion a quantity of the first type of seed from the bulk supply 426 of the first type of seed for use in preparing the seed mix. For example, the bulk supply 426 of the first type of seed may include transgenic seeds each having substantially a size of AF2. And, because the seeds have substantially the same size, a precise quantity of the first type of seed may be portioned by the first dispensing assembly by releasing, dumping, and/or poring a specific weight (e.g., a predetermined weight based on the particular size of the seed (e.g., AF2, etc.), a predetermined weight based on the particular type of seed, etc.) of the seeds into a receiving container (not shown) of the first dispensing assembly 422.

More particularly, the first dispensing assembly 422 is operable to provide a quantity of the first type of seeds to a weighing mechanism (not shown), which is associated with the receiving container of the first dispensing assembly, to thereby portion a quantity of the first type of seed from the bulk supply 426. For example, the first dispensing assembly 422 may operate to fill the receiving container with seeds until the weighing mechanism indicates that a desired weight is achieved (indicative of a particular number of the first type of seeds). The weighing mechanism may then operate to confirm that an accurate quantity of the first type of seed has been portioned.

The illustrated system 420 also includes a second dispensing assembly 424 disposed adjacent the bulk supply 428 of the second type of seed. The second dispensing assembly 424 is configured to portion a quantity of the second type of seed from the bulk supply 428 of the second type of seed for use in preparing the seed mix. As with the bulk supply 426 of the first type of seed, the bulk supply 428 of the second type of seed includes seeds having substantially the same size (within industry recognized tolerances). In addition (although not required), the second type of seeds may have substantially the same size as the first type of seeds.

With additional reference to FIG. 11, the second dispensing assembly 424 includes a funnel 490, which generally directs the second type of seed (indicated at S in FIG. 11) from the bulk supply 428 to a vibrating platform 491. The vibrating platform 491 vibrates to thereby move seeds received through the funnel 490 to respective bins 492. The bins 492 are disposed generally circumferentially around an outer perimeter of the vibrating platform 491 and are configured to receive and/or retain the seeds. Guides 493 are coupled to the vibrating platform 491 to help direct, guide, etc. the seeds into the bins 492. The bins 492 are associated with one or more weighing mechanisms (e.g., scales, etc.) (not shown) to ensure that a precise quantity of the second type of seed is portioned into each of the bins 492. The desired weight may be associated with, or indicative of, a particular number of the second type of seed (e.g., based on an average density of the second type of seed in the bulk supply 428, etc.). And, as the bins 492 are being filled with seeds, when the weighing mechanism associated with a bin 492 indicates that a desired weight has been reached (e.g., a weight associated with a desired quantity of the seeds, etc.), the bin 492 transfers the seeds retained therein to a conveyor assembly 444 for subsequent transport. As such, the second dispensing assembly 424 has portioned a quantity of the second type of seed from the bulk supply 428. Alternatively, the bins 492 may be filled with seeds, and a program may select which bin 492 most closely matches a desired weight and transfer the seeds from that bin to the conveyor assembly 444.

With further reference to FIG. 12, the illustrated conveyor assembly 444 generally includes a delivery sub-assembly 494 positioned proximal the packaging assembly 432. The delivery sub-assembly 494 includes a number of different paths and valves generally leading to the packaging assembly 432, to help ensure that each portioned quantity of the second type of seed received from the second dispensing assembly 424 is preserved until delivery to the packaging assembly 432. It should be appreciated that different numbers of paths and/or valves, and/or different components (e.g., tubes, pipes, channels, chutes, troughs, hoses, slides, etc.) may be included in the delivery sub-assembly 494 within the scope of the present disclosure.

The illustrated delivery sub-assembly 494 generally includes four different sets of tubes 495, suitable, for example, for staging four separate portioned quantities of the second type of seed received from the second dispensing assembly that are to be combined with the first type of seed received from the first dispensing assembly 422 (FIG. 10). In this manner, the system 420 may help ensure that a portioned quantity of the second type of seed is consistently available to be combined with a portioned quantity of the first type of seed. In addition, a portioned quantity of the second type of seed may be released from a respective one of the tubes 495 at about the same time that a first type of seed is released from the first dispensing assembly 422 so that the first and second types of seed may be generally mixed, blended, etc. as they are dispensed into the packaging assembly 432.

The illustrated delivery sub-assembly 494 also includes a return path 460, which may be employed to empty unwanted quantities of seed from the conveyor assembly 444 (e.g., based on analysis (e.g., visual analysis, etc.) of the seeds taking place along a path of the conveyor assembly 444 and/or at the delivery sub-assembly 494, etc.), misfed quantities of seed from the conveyor assembly, etc. The return path 460 may empty the quantity of seed into a bin 464 for recycling into the system 420, for storage, for disposal, etc.

The packaging assembly 432 includes two chutes 496 and 497 each configured to receive and hold a portioned quantity of the first type of seed (received from the first dispensing assembly 422) together with a portioned quantity of the second type of seed (received from the second dispensing assembly 424 (via the delivery sub-assembly 494). Each chute 496 and 497 is thereby configured to receive portioned quantities of both the first and second types of seeds together within the chute 496 and 497. In addition, the portioned quantities of the first and second types of seeds can be delivered to each of the chutes (e.g., either chute 496 or chute 497, etc.) at about the same time such that the first and second types of seed may be generally mixed, blended, etc. together within the given chute (e.g., within chute 496 or chute 497, etc.) (e.g., such that the first and second types of seeds are blended in the total quantity, etc.). And, the combined portioned quantities of the first and second types of seeds received within the given chute (e.g., within chute 496 or within chute 497, etc.) ultimately provides a total quantity of first and second types of seeds that is substantially equal to a target quantity of seeds, and that has a ratio of the first type of seed to the second type of seed that is substantially equal to a predetermined value.

The chutes 496 and 497 each include a pair of doors 498 selectively operable between a closed position to allow the chutes 496 and 497 to be filled with the combined quantities of the first and second types of seeds, and an open position to allow the chutes to release the seeds. The doors 498 are initially closed to allow the chutes 496 and 497 to fill with the combined quantities of the first and second types of seeds. The doors 498 may then be opened to allow the combined first and second types of seeds to be released from the chutes 496 and 497 into respective packages (not shown). In the illustrated embodiment, the seeds fall from the chutes 496 and 497 via gravity, further mixing, blending, etc. the first and second types of seeds. In other example embodiments, packaging assemblies may include one or more chutes structured without doors to directly pass seeds through the chutes (and thus so as not to retain combined seeds in the chutes) from dispensing assemblies into packages.

In the illustrated embodiment, the chutes 496 and 497 are operated generally in series, such that only one of the chutes 496 or 497 releases combined seeds into a package at any one time. While one of the chutes 496 or 497 is releasing combined seeds into a package, the other chute 496 or 497 is being filled with seeds from the first and second dispensing assemblies 422 and 424. This ultimately provides a generally sequential, series, etc. operation of the chutes 496 and 497.

In other example embodiments, weighing devices (e.g., scales, etc.) may be associated with the chutes 496 and/or 497 to further weight quantities of the first and/or second types of seeds as they are transferred to the chutes 496 and/or 497.

Figure 13:
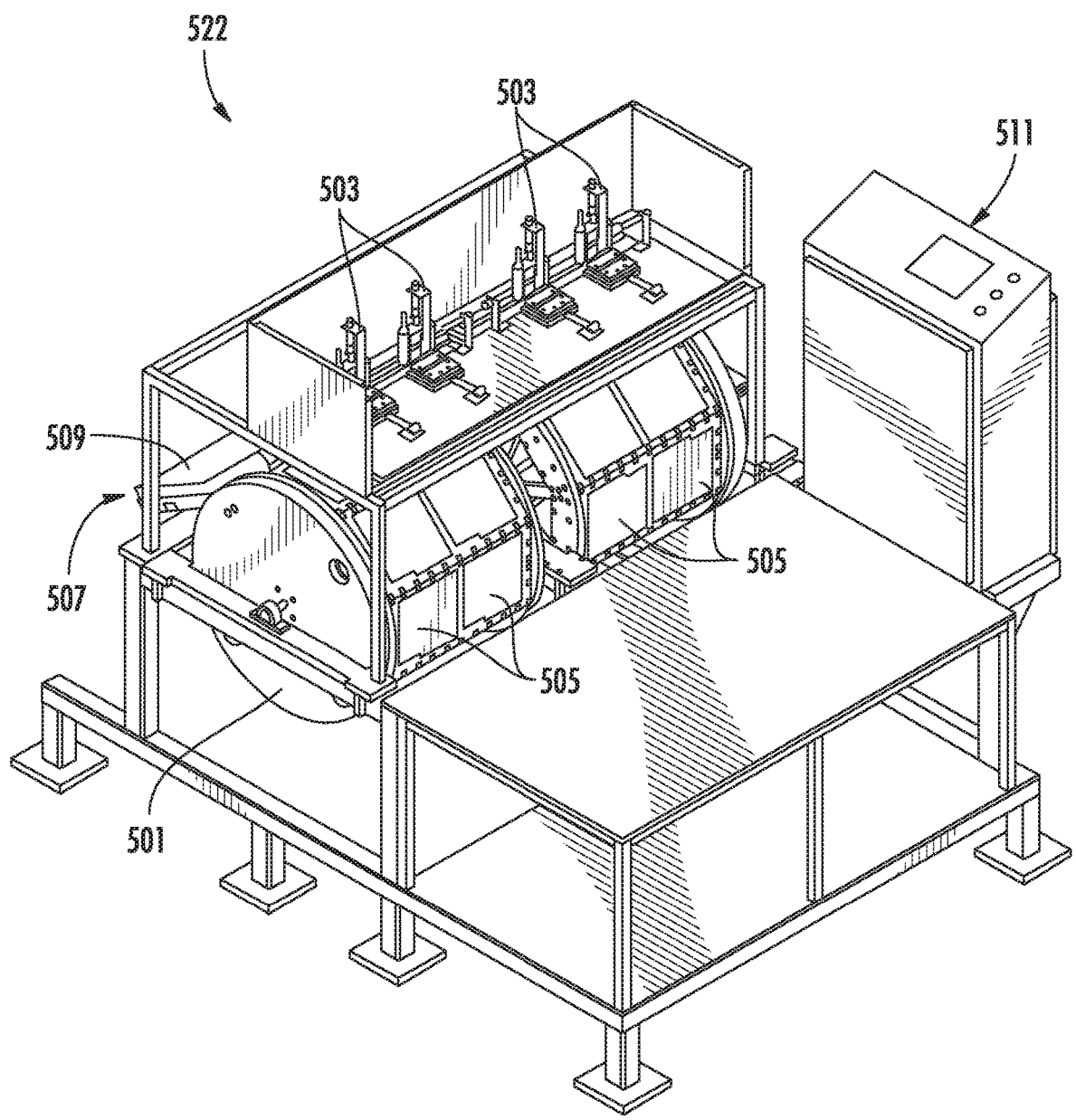
FIG. 13 is a perspective view of an example dispensing assembly including one or more aspects of the present disclosure.

FIG. 13 illustrates an example embodiment of a dispensing assembly 522 suitable for use with one or more of the systems previously described. The dispensing assembly 522 is configured to portion a quantity of a type of seed from a bulk supply of the type of seed. The illustrated dispensing assembly 522 includes drums 501, imaging detectors 503 disposed adjacent to the drums 501, and seed trays 505 disposed generally around the drums 501. In other example embodiments, dispensing assemblies may include configurations and/or numbers of drums, imaging detectors, and/or seed trays different than disclosed herein.

The dispensing assembly 522 of this embodiment is configured to receive seeds in the seed trays 505 disposed around the drums 501. The seeds are held in place in the seed trays 505 via a vacuum. The detectors 503 are then operable to image the seed trays 505 (or a portion thereof) and count the number of seeds present in the imaged seed trays 505, and then determine if an acceptable number of seeds are present in the imaged seed trays 505. If an acceptable number of seeds are present, the vacuum is released and the seeds are removed by seed removal device 507 via passage 509 for collection in a container (not shown). As the seeds are released, a count may be incremented so as to provide a precise total count of the quantity of seeds ejected into the container.

The dispensing assembly 522 may be managed and/or controlled by a control sub-assembly 511.

Example methods (e.g., process 2, etc.) systems (e.g., system 120, 220, 320, 420, etc.) of the present disclosure generally provide for mixing, blending, etc. of the first and second types of seeds, for example, when the seeds are transferred into weigh buckets of seed mixing assemblies, as well as when the seeds are dispensed from the weigh buckets to packaging assemblies, etc. As such, the methods and systems may be viewed as providing blended seed mixes for packaging in which the seeds are generally uniformly mixed throughout the packages. In this manner, segregation of the first and second types of seeds within the packages may be minimized, and a semi-uniform or uniform dispersal of the first and second types of seed may be achieved within the packages. Moreover, once the total quantity of combined first and second types of seeds is within a package, the package is sealed and transported (e.g., via conveyor assemblies, transport machinery, etc.) for storage, delivery, planting, etc. In this manner, the methods and systems combine (e.g., mix, blend, etc.) the portioned quantities of the first and second types of seeds as desired directly and immediately before the seeds are sealed within the packages without further processing. In other example embodiments, systems may include active blending devices to help further ensure generally uniform dispersal of different types of seeds within packages.

Example methods (e.g., process 2, etc.) and systems (e.g., system 120, 220, 320, 420, etc.) of the present disclosure may be used to package single types of seeds within the scope of the present disclosure. For example, the example methods and systems may be used to package first types of seeds without second types of seeds (e.g., the methods and systems may be operated so that only the first types of seeds are delivered to the packages, with the second types of seeds bypassing the packages, etc.).

Seed mixes prepared in accordance with the present disclosure provide repeatable, accurate seed mixes each having about a target quantity of seeds and each having about a target ratio of seeds. For example, the total quantity of seeds in each final package prepared by the example processes and systems may be counted (e.g., via weight correlations such that the total quantity of seeds in each package is weighed, etc.). As such, the total quantity of seeds in each package and the ratio of different types of seeds in each package is generally consistent from package to package such that methods and systems of the present disclosure can provide reproducible, accurate outputs for each seed mix (and for each package including a seed mix).

In addition, seed mixes prepared in accordance with the present disclosure can have two or more different types of seeds including, for example, transgenic seeds and refuge seeds. As such, the seed mixes can be used in seed mix refuge strategies as part of insecticide resistance management (IRM) programs. Seed mix refuge strategies describe operations for deploying into a field of crops some percentage of refuge seeds which sprout and develop into mature refuge plants that allow certain pests to surface (and to which plants grown from the transgenic seeds are resistant). Thus, the seed mixes can be packaged to provide a refuge in a bag to farmers that, when planted, provide tools for delaying or possibly eliminating onset of resistance development to properties and/or expressions not shared between types of seeds included in the seed mixes. The RIB is one way of ensuring that all transgenic insect protected crop fields have associated refuge lacking insect protection. By blending insect protected seed with unprotected seed, refuge will be present in all fields independent of the product selected by a particular farmer.

Further, seed mixes prepared in accordance with the present disclosure may provide yield protection and/or may lead to increased yields relative to planting the same proportion of unprotected seed as a separate block (i.e., in a traditional structured refuge). This can occur because unprotected plants in a field planted with an unstructured refuge will tend to be surrounded by insect-protected plants. This will decrease the average amount of damage occurring to unprotected plants because there will not be larvae moving over from other adjacent unprotected plants, as there would be in a block refuge and pest populations will tend to be smaller. Smaller pest populations on unprotected plants can mean less damage and higher yields.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A process for repeatedly preparing seed mixes each having a target quantity and a target ratio of different types of seeds, the process comprising:
portioning first and second quantities of a first type of seed from a bulk supply of the first type of seed;
delivering the first portioned quantity of the first type of seed to a first compartment of a seed mixing assembly and delivering the second portioned quantity of the first type of seed to a second compartment of the seed mixing assembly;
portioning first and second quantities of a second type of seed from a bulk supply of the second type of seed;
delivering the first portioned quantity of the second type of seed to the first compartment of the seed mixing assembly and delivering the second portioned quantity of the second type of seed to the second compartment of the seed mixing assembly;
for the first portioned quantities of the first and second types seeds delivered to the first compartment:
combining, by the seed mixing assembly, the portioned quantities of the first and second types of seeds in the first compartment of the seed mixing assembly to prepare a first seed mix;
wherein the combined quantities of the first and second types of seeds in the first seed mix are substantially equal to a target quantity for the first seed mix, and wherein a ratio of the quantity of the first type of seed to the quantity of the second type of seed in the first seed mix is substantially equal to a target ratio for the first seed mix; and
for the second portioned quantities of the first and second types of seeds delivered to the second compartment:
combining, by the seed mixing assembly, the portioned quantities of the first and second types of seeds in the second compartment of the seed mixing assembly to prepare a second seed mix;
wherein the combined quantities of the first and second types of seeds in the second seed mix are substantially equal to a target quantity for the second seed mix, and wherein a ratio of the quantity of the first type of seed to the quantity of the second type of seed in the second seed mix is substantially equal to the target ratio for the second seed mix.

2. The process of claim 1, wherein portioning the first and second quantities of the first type of seed includes portioning a specific weight of the first type of seed from the bulk supply of the first type of seed;
wherein portioning the first and second quantities of the second type of seed includes portioning a specific weight of the second type of seed from the bulk supply of the second type of seed; and
wherein the specific weight of the first type of seed is associated with the quantity of the first type of seed to be included in the seed mix, and the specific weight of the second type of seed is associated with the quantity of the second type of seed to be included in the seed mix.

3. The process of claim 1, wherein delivering each of the first and second portioned quantities of the first type of seed to the respective first and second compartments of the seed mixing assembly includes transferring the first type of seed to the respective compartment until a specific weight of the first type of seed is received in the respective compartment.

4. The process of claim 1, further comprising delivering, by the seed mixing assembly, the first seed mix to a first seed package and delivering the second seed mix to a second seed package.

5. The process of claim 4, wherein the combined quantities of the first and second types of seeds in the first seed package are substantially equal to the combined quantities of the first and second types of seeds in the second seed package, and where the ratio of the quantity of the first type of seed to the quantity of the second type of seed in the first seed package is substantially equal to the ratio of the quantity of the first type of seed to the quantity of the second type of seed in the second seed package.

6. The process of claim 5, wherein the target ratio of the quantity of the first type of seed to the quantity of the second type of seed for each of the first and second seed mixes is between about 4:1 and about 39:1 and/or wherein the target quantity of combined seeds for each of the first and second seed mixes is between about 50,000 and about 5 million.

7. The process of claim 1, wherein the first type of seed is a transgenic seed and the second type of seed is a refuge seed.

8. The process of claim 1, wherein the first type of seed and/or the second type of seed is a transgenic seed comprising at least one transgene conferring at least one of herbicidal tolerance and pest resistance to the seed.

9. The process of claim 1, wherein portioning the first and second quantities of the first and second types of seeds and combining the first and second portioned quantities are performed by an automated seed blending system comprising the seed mixing assembly.

10. The process of claim 1, further comprising:
portioning first and second quantities of at least a third type of seed;
combining the first portioned quantity of the at least third type of seed with the first portioned quantities of the first and second types of seeds; and
combining the second portioned quantity of the at least third type of seed with the second portioned quantities of the first and second types of seeds.

11. The process of claim 1, wherein delivering the first portioned quantity of the first type of seed to the first compartment of the seed mixing assembly includes directing part of the first portioned quantity of the first type of seed to the first compartment through a first chute and directing another part of the first portioned quantity of the first type of seed to the first compartment through a second chute.

12. The process of claim 1, further comprising:
processing the first type of seed so that each seed in the first and second portioned quantities of the first type of seed has about the same size; and/or
processing the second type of seed so that each seed in the first and second portioned quantities of the second type of seed has about the same size.

13. The process of claim 1, further comprising:
processing the first type of seed so that each seed in the first and second portioned quantities of the first type of seed has the same color; and/or
processing the second type of seed so that each seed in the first and second portioned quantities of the second type of seed has the same color.

14. A process for combining different types of seeds, the process comprising:
providing first and second types of seeds to be included in a seed mix;
weighing a quantity of the second type of seed;
transferring the weighed quantity of the second type of seed to a container;
transferring the first type of seed to the container and concurrently weighing a combined quantity of the first and second types of seeds in the container;
determining whether a specific weight of the first type of seed has been received in the container based on the weight of the quantity of the second type of seed transferred to the container and the weight of the combined quantity of the first and second types of seeds in the container; and
in response to a determination that the specific weight of the first type of seed has been received in the container, stopping transfer of the first type of seed to the container;
wherein the combined quantity of the first and second types of seeds in the container is substantially equal to a target quantity, and wherein a ratio of the quantity of the first type of seed in the container to the quantity of the second type of seed in the container is substantially equal to a target ratio.

15. The process of claim 14, wherein the first type of seed is a transgenic seed and the second type of seed is a refuge seed.

16. The process of claim 14, further comprising:
providing a third type of seed to be included in the seed mix;
weighing a quantity of the third type of seed; and
transferring the weighed quantity of the third type of seed to the container;
wherein a combined quantity of the first, second, and third types of seeds in the container is substantially equal to a target quantity, and wherein a ratio of the quantity of the first type of seed in the container to the quantity of the second type of seed in the container to the quantity of the third type of seed in the container is substantially equal to a target ratio.

17. The process of claim 14, further comprising:
providing a third type of seed to be included in the seed mix; and
transferring the third type of seed to the container and concurrently weighing a combined quantity of the first, second, and third types of seeds in the container;
wherein the combined quantity of the first, second, and third types of seeds in the container is substantially equal to a target quantity, and wherein a ratio of the quantity of the first type of seed in the container to the quantity of the second type of seed in the container to the quantity of the third type of seed in the container is substantially equal to a target ratio.

18. A process for combining different types of seeds into a seed mix, the process comprising:
portioning a quantity of a first type of seed from a bulk supply of the first type of seed;
delivering, by a first dispensing assembly, the portioned quantity of the first type of seed to a seed mixing assembly;
portioning a quantity of a second type of seed from a bulk supply of the second type of seed and delivering, by a second dispensing assembly, the portioned quantity of the second type of seed to a hopper;
analyzing the portioned quantity of the second type of seed;
when the analysis indicates that the portioned quantity of the second type of seed is acceptable for the seed mix, delivering the portioned quantity of the second type of seed from the hopper to the seed mixing assembly;
when the analysis indicates that the portioned quantity of the second type of seed is not acceptable for the seed mix, emptying the portioned quantity of the second type of seed from the hopper through a return to a storage bin, without delivering the portioned quantity of the second type of seed to the seed mixing assembly, whereby the portioned quantity of the second type of seed is received in the storage bin instead of at the seed mixing assembly and is maintained separate from the first type of seed; and
when the portioned quantity of the second type of seed is delivered to the seed mixing assembly, combining, by the seed mixing assembly, the portioned quantities of the first and second types of seeds to prepare the seed mix, wherein the combined quantities of the first and second types of seeds in the seed mix are substantially equal to a target quantity, and wherein a ratio of the quantity of the first type of seed to the quantity of the second type of seed is substantially equal to a target ratio.

19. The process of claim 1, wherein the first and second quantities of the first type of seed each include the same quantity of the first type of seed; and wherein the first and second quantities of the second type of seed each include the same quantity of the second type of seed.

* * * * *